United States Patent
Kim et al.

(10) Patent No.: US 7,118,913 B2
(45) Date of Patent: Oct. 10, 2006

(54) EXPRESSION VECTOR CONTAINING UREA CYCLE ENZYME GENE, TRANSFORMANT THEREOF, AND USE OF TRANSFORMANT FOR PROTEIN OVER-EXPRESSION

(75) Inventors: Hong-Jin Kim, Incheon (KR); Myung-Il Chung, Gwacheon (KR); Ik-Hwan Kim, Seoul (KR); Ick-Young Kim, Seoul (KR)

(73) Assignee: Chung-Ang University Industry Academic Cooperation Foundation, Seoul (KR)

( * ) Notice: Subject to any disclaimer, the term of this patent is extended or adjusted under 35 U.S.C. 154(b) by 495 days.

(21) Appl. No.: 10/363,421

(22) PCT Filed: Aug. 24, 2001

(86) PCT No.: PCT/KR01/01434

§ 371 (c)(1),
(2), (4) Date: Feb. 25, 2003

(87) PCT Pub. No.: WO02/16626

PCT Pub. Date: Feb. 28, 2002

(65) Prior Publication Data

US 2005/0089849 A1    Apr. 28, 2005

(30) Foreign Application Priority Data

Aug. 25, 2000  (KR) ............... 2000-49688
Aug. 20, 2001  (KR) ............... 2001-50083

(51) Int. Cl.
*C12N 5/06* (2006.01)
*C12N 15/63* (2006.01)

(52) U.S. Cl. .............. 435/362; 435/358; 435/320.1; 536/23.5; 536/23.1; 536/23.2

(58) Field of Classification Search ........... 435/410, 435/320.1, 183
See application file for complete search history.

(56) References Cited

FOREIGN PATENT DOCUMENTS

WO    WO 97/30167    * 8/1997

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*
Yang and Butler, Biotechnol. Bioeng., vol. 69, pp. 370-380, May 2000.*
Cayli, et al., "Cell Lines With Reduced UDP-N-Acetylhexosamine Pool in the Presence of Ammonium", *Biotechnology and Bioengineering*, No. 2, vol. 65, pp. 192-200 (1999).

(Continued)

*Primary Examiner*—Richard Hutson
(74) *Attorney, Agent, or Firm*—Abelman, Frayne & Schwab

(57) ABSTRACT

The present invention relates to expression vectors containing in vivo urea cycle enzyme gene; transformants thereof; and the use of transformants for protein overexpression. During the overexpression of protein, if the animal cell transformed with expression vectors of the present invention is used, amounts of ammonia accumulation within cell culture medium will decrease and cell growth rate will increase, thus, it is advantageous to be capable of obtaining desired protein in high yields.

10 Claims, 14 Drawing Sheets

OTHER PUBLICATIONS

Zanghi, et al., "Role of Nucleotide Sugar Pools in the Inhibition of NCAM Polysialylation by Ammonia", *Biotechnol. Prog.*, vol. 14, pp. 834-844 (1998).

Jeong, et al., "Ammonium Ion Effects and Its In Situ Removal by Using Immobilized Adsorbent in Hybridoma Cell Culture", *Korean Journal Biotechnol. Bioengineering*, vol. 11, No. 3, pp. 329-339 (1996).

Chang, et al., "In-Situ Removal of Ammonium and Lactate through Electrical Means for Hybridoma Cultures", *Biotechnology and Bioengineering*, vol. 47, pp. 308-318 (1995).

Chang, et al., "Nutrient Enrichment and In-Situ Waste Removal through Electrical Means for Hybridoma Cultures", *Biotechnology and Bioengineering*, vol. 47, pp. 319-326 (1995).

Capiaumont, et al., "Methods for reducing the ammonia in hybridoma cell cultures", *Journal of Biotechnology*, vol. 39, pp. 49-58 (1995).

Hansen, et al., "Influence of Ammonium on Growth, Metabolism, and Productivity of a Continuous Suspension Chinese Hamster Ovary Cell Culture", *Biotechnol. Prog.*, vol. 10, pp. 121-124 (1994).

Nayve, Jr., et al., "HBs-MAb production in perfusion culture with selective ammonia removal system", *Journal of Biotechnology*, vol. 34, pp. 217-225 (1994).

Schneider, et al., "Principles of an efficient new method for the removal of ammonia from animal cell cultures using hydrophobic membranes", *Enzyme Microb. Technology*, vol. 16, pp. 957-963 (Nov. 1994).

Atanassov, et al., "Effect of ammonia on endocytosis, cytokine production and lysosomal enzyme activity of a microglial cell line", *Res. Immunol.*, vol. 145, pp. 277-288 (1994).

Fitzpatrick, et al., "Glucose and Glutamine Metabolism of a Murine B-Lymphocyte Hybridoma Grown in Batch Culture", *Applied Biochemistry and Biotechnology*, vol. 43, pp. 93-116 (1993).

Racher, et al., "Influence of ammonium ion and glucose on mAb production in suspension and fixed bed hybridoma cultures", *Journal of Biotechnology*, vol. 29, pp. 145-156 (1993).

Bushell, et al., "A Three-Phase Pattern in Growth, Monoclonal Antibody Production, and Metabolite Exchange in a Hybridoma Bioreactor Culture", *Biotechnology and Bioengineering*, vol. 42, pp. 133-139 (1993).

Hiller, et al., "Transient Responses of Hybridoma Cells in Continuous Culture to Step Changes in Amino Acid and Vitamin Concentrations", *Biotechnology and Bioengineering*, vol. 44, pp. 303-321 (1994).

Hassell, et al., "Growth Inhibition in Animal Cell Culture The Effect of Lactate and Ammonia", *Applied Biochemistry and Biotechnology*, vol. 30, pp. 29-41, (1991).

McQueen, et al., "Growth inhibition of hybridoma cells by ammonium ion: correlation with effects on intracellular pH", *Bioprocess Engineering*, vol. 6, pp. 49-61 (1991).

Ozturk, et al., "Chemical Decomposition of Glutamine in Cell Culture Media: Effect of Media Type, pH, and Serum Concentration", *Biotechnol. Prog.*, vol. 6, No. 2, pp. 121-128 (1990).

Hassell, et al., "Adaptation to non-ammoniagenic medium and selective substrate feeding lead to enhanced yields in animal cell cultures", *Journal of Cell Science*, vol. 96, pp. 501-508 (1990).

Meijer, et al., "Nitrogen Metabolism and Ornithine Cycle Function", *Physiological Review*, vol. 70, pp. 701-748 (1990).

Newland, et al., "Hybridoma growth limitations: The roles of energy metabolism and ammonia production", *Cytotechnology*, vol. 3, pp. 215-229 (1990).

Doyle, et al., "The effect of pH on the toxicity of ammonia to a murine hybridoma", *Journal of Biotechnology*, vol. 15, pp. 91-100 (1990).

Kurano, et al., "Growth behavior of Chinese hamster ovary cells in a compact loop bioreactor. 2. Effects of medium components and waste products", *Journal of Biotechnology*, vol. 15, pp. 113-128 (1990).

McQueen, et al., "Mathematical Modeling of the Effects of Ammonium Ion on the Intracellular pH of Hybridoma Cells", *Biotechnology and Bioengineering*, vol. 35, pp. 897-906 (Apr. 1990).

Wakisaka, et al., "A Rapid Assay Method for Ammonia Using Glutamine Synthetase from Glutamate-Producing Bacteria", *Analytical Biochemistry*, vol. 163, pp. 117-122 (1987).

Sheffield, et al., "Expression in *Escherichia coli* of Functional Precursor to the Rat Liver Mitochondrial Enzyme, Ornithine Carbamyl Transferase. Precursor Import and Processing In Vitro", *Biochemical and Biophysical Research Communications*, vol. 134, No. 1, pp. 21-28 (Jan. 14, 1986).

Reuveny, et al., "Factors affecting cell growth and monoclonal antibody production in stirred reactors", *Journal of Immunological Methods*, vol. 86, pp. 53-59 (1986).

Glacken, et al., "Reduction of Waste Product Excretion via Nutrient Control: Possible Strategies for Maximizing Product and Cell Yields on Serum in Cultures of Mammalian Cells", *Biotechnology and Bioengineering*, vol. XXVIII, pp. 1376-1389 (Sep. 1986).

Butler, et al., "The effects of glutamine utilisation and ammonia production on the growth of BHK cells in microcarrier cultures", *Journal of Biotechnology*, vol. 1, pp. 187-196 (1984).

Moreadith, et al., "The Pathways of Glutamate and Glutamine Oxidation by Tumor Cell Mitochondria Role of Mitochondrial Nad(P)—Dependent Malic Enzyme", *The Journal of Biological Chemistry*, vol. 259, No. 10, Issue of May 25, pp. 6215-6221 (1984).

Butler, et al., "High Yields From Microcarrier Cultures by Medium Perfusion", *J. Cell. Sci.*, vol. 61, pp. 351-363 (1983).

Mori, et al., "Ornithine transcarbamylase in liver mitochondria", *Molecular and Cellular Biochemistry*, vol. 49, pp. 97-111 (1982).

Powers, "Regulation of Rat Liver Carbamyl Phosphate Synthetase I Inhibition by Metal Ions and Activation by Amino Acids and Other Chelating Agents", *The Journal of Biological Chemistry*, vol. 256, No. 21, pp. 11,160-11,165 (Nov. 10, 1981).

Ito, et al., "Ammonia Inhibition of Interferon Synthesis", *Cell Biology International Reports*, vol. 5, No. 7 pp. 661-666 (Jul. 1981).

Karin, et al., "Receptor-mediated Endocytosis of Transferrin in Developmentally Totipotent Mouse Teratocarcinoma Stem Cells", *The Journal of Biological Chemistry*, vol. 256, No. 7, pp. 3245-3252 (Apr. 10, 1981).

King, et al., "Lysomotropic amines cause intracellular accumulation of receptors for epidermal growth factor", *Proc. Natl. Acad. Sci. USA*, vol. 77, No. 6, pp. 3283-3287 (Jun. 1980).

Van Leuven, et al., "Primary Amines Inhibit Recycling of $\alpha_2 M$ Receptors in Fibroblasts", *Cell*, vol. 20, pp. 37-43 (May 1980).

Commoy-Chevalier, et al., "Effect of Ammonium Salts on the Interferon-induced Antiviral State in Mouse L Cells", *J. Gen. Virol*, vol. 41, pp. 541-547 (1978).

Boron, et al., "Intracellular pH Transients in Squid Giant Axons Caused by $CO_2$, $NH_3$, and Metabolic Inhibitors", *The Journal of General Physiology*, vol. 67, pp. 91-112 (1976).

Visek, et al., "Ammonia Effects in Cultures of Normal and Transformed 3T3 Cells", *J. Cell. Physiol.*, vol. 80, pp. 373-382 (1972).

Kim, et al., "Ammonia Intoxication in Rats: Protection by N-Carbamoyl-$_L$-Glutamate Plus $_L$-Arginine" *Proc. Nat. Acad. Sci. USA*, vol. 69, No. 12, pp. 3530-3533 (Dec. 1972).

Stone, et al., "Pathways of Ammonia Metabolism in the Intact Functioning Kidney of the Dog", *Journal of Clinical Investigation*, vol. 46, No. 7, pp. 1141-1150 (1967).

Ryan, et al., "Amino Acids and Ammonia of Fetal Calf Serum During Storage", *Storage of Fetal Calf Serum PSEBM vol. 123*, pp. 27-30 (1966).

Fahien, et al., "Studies on the Mechanism of Action of Acetylglutamate as an Activator of Carbamyl Phosphate Synthetase," *The Journal of Biological Chemistry*, vol. 239, No. 6, pp. 1935-1941 (Jun. 1964).

Tritsch, et al., "Spontaneous Decomposition of Glutamine in Cell Culture Media", *Experimental Cell Research*, vol. 28, pp. 360-364 (1962).

Eaton, et al., "Inhibition by Ammonium Ion of the Growth of Influenza Virus in Chorioallantoic Tissue", *Vitrology*, vol. 18, pp. 102-108 (1962).

Furusawa, et al., Inhibitory Effecct of Ammonium Sulfate on Columbia SK Virus Propagation in Mouse Ascites Tumor Cells *in vitro, PSEBM*, vol. 111, pp. 71-75 (1962).

Greenstein & Winitz, *Chemistry of the Amino Acids*, "Chapter 20—Enzymes Involved in the Determination, Characterization, & Preparation of the Amino Acids", vol. 2, pp. 1751-1758 (Wiley, New York 1961).

Eaton, et al., "Inhibitory Effect of Glutamine and Ammonia on Replication of Influenza Virus in Ascites Tumor Cells", *Virology*, vol. 13, pp. 300-307 (1961).

Jensen, et al., "Studies of Inhibitory Effect of Ammonium Ions in Several Virus-Tissue Culture Systems", *P.S.E.B.M.*, vol. 107, pp. 834-838 (1961).

Darnell, Jr., "Glucose and Glutamine in Poliovirus Production by HeLa Cells", *Virology*, vol. 6, pp. 556-566 (1958).

Grisolia, et al., "Catalytic Role of Glutamate Derivatives in Citrulline Biosynthesis", *Laboratory of Physiological Chemistry, University of Wisconsin*, pp. 753-757 (1953).

Ozturk et al., "Effects of Ammonia and Lactate on Hybridoma Growth, Metabolism, and Antibody Production", *Biotechnology and Bioengineering*, vol. 39, pp. 418-431 (1992).

Bray et al., "The Enzymic Hydrolysis of Glutamine and its Spontaneous Decomposition in Buffer Solutions", *Biochemistry*, vol. 44, pp. 625-627, (1949).

Pierson et al., "Human Ornithine Transcarbamylase—Purification and Characterization of the Enzyme from Normal Liver and the Liver of a Reye's Syndrome Patient", *The Journal of Biological Chemistry*, vol. 252, No. 18, pp. 6464-6469, (1977).

\* cited by examiner

SEQUENCE LISTING

<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: forward primer for identification of rat CPS 1
      expression level

<400> SEQUENCE: 1
atgctttctg tgaaggcaca g                                           21

<210> SEQ ID NO 2
<211> LENGTH: 20
<212> TYPE: DNA
<213> ORGANISM: Artificial Sequence
<220> FEATURE:
<223> OTHER INFORMATION: backward primer for identification of rat CPS 1
      expression level

<400> SEQUENCE: 2
gggctgacct ctgggtggaa                                             20

<210> SEQ ID NO 3
<211> LENGTH: 18
<212> TYPE: DNA
<213> ORGANISM: Artificial Sequence
<220> FEATURE:
<223> OTHER INFORMATION: forward primer for rat OTC cloning and
      identification of OTC expression level

<400> SEQUENCE: 3
atgctgtcta atttgagg                                               18

<210> SEQ ID NO 4
<211> LENGTH: 18
<212> TYPE: DNA
<213> ORGANISM: Artificial Sequence
<220> FEATURE:
<223> OTHER INFORMATION: backward primer for rat OTC cloning and
      identification of OTC expression level

<400> SEQUENCE: 4
tcagaacttt ggcttctg                                               18

<210> SEQ ID NO 5
<211> LENGTH: 18
<212> TYPE: DNA
<213> ORGANISM: Artificial Sequence
<220> FEATURE:
<223> OTHER INFORMATION: forward primer for rat AS cloning

<400> SEQUENCE: 5
caagatgtcc agcaaggg                                               18

<210> SEQ ID NO 6
<211> LENGTH: 18
<212> TYPE: DNA
<213> ORGANISM: Artificial Sequence
<220> FEATURE:
<223> OTHER INFORMATION: backward primer for rat AS cloning

<400> SEQUENCE: 6
ctatttggcg gtgacctt                                               18

-continued

<210> SEQ ID NO 7
<211> LENGTH: 18
<212> TYPE: DNA
<213> ORGANISM: Artificial Sequence
<220> FEATURE:
<223> OTHER INFORMATION: forward primer for rat Arg cloning and
      identification of Arg expression level

<400> SEQUENCE: 7
gagcatgagc tccaagcc                                                 18

<210> SEQ ID NO 8
<211> LENGTH: 18
<212> TYPE: DNA
<213> ORGANISM: Artificial Sequence
<220> FEATURE:
<223> OTHER INFORMATION: backward primer for rat Arg cloning and
      identification of Arg expression level

<400> SEQUENCE: 8
ttatttcggt ggtttaag                                                 18

<210> SEQ ID NO 9
<211> LENGTH: 18
<212> TYPE: DNA
<213> ORGANISM: Artificial Sequence
<220> FEATURE:
<223> OTHER INFORMATION: forward primer for identification of rat AS
      expression level

<400> SEQUENCE: 9
cagtccagtg cactctat                                                 18

<210> SEQ ID NO 10
<211> LENGTH: 18
<212> TYPE: DNA
<213> ORGANISM: Artificial Sequence
<220> FEATURE:
<223> OTHER INFORMATION: backward primer for identification of rat AS
      expression level

<400> SEQUENCE: 10
ccagaaaccg gtgtataa                                                 18

<210> SEQ ID NO 11
<211> LENGTH: 18
<212> TYPE: DNA
<213> ORGANISM: Artificial Sequence
<220> FEATURE:
<223> OTHER INFORMATION: forward primer for identification of rat AL
      expression level

<400> SEQUENCE: 11
acgtgatgtt ctcttccc                                                 18

<210> SEQ ID NO 12
<211> LENGTH: 18
<212> TYPE: DNA
<213> ORGANISM: Artificial Sequence
<220> FEATURE:
<223> OTHER INFORMATION: backward primer for identification of rat AL
      expression level

<400> SEQUENCE: 12
ggccatgaac acagcttt                                                 18

```
<210> SEQ ID NO 13
<211> LENGTH: 18
<212> TYPE: DNA
<213> ORGANISM: Artificial Sequence
<220> FEATURE:
<223> OTHER INFORMATION: forward primer for rat CPS 1 cloning

<400> SEQUENCE: 13
atgacgagga ttttgaca                                                 18

<210> SEQ ID NO 14
<211> LENGTH: 18
<212> TYPE: DNA
<213> ORGANISM: Artificial Sequence
<220> FEATURE:
<223> OTHER INFORMATION: backward primer for rat CPS 1 cloning

<400> SEQUENCE: 14
gctcctgctg actgaagg                                                 18
```

EXPRESSION VECTOR CONTAINING UREA CYCLE ENZYME GENE, TRANSFORMANT THEREOF, AND USE OF TRANSFORMANT FOR PROTEIN OVER-EXPRESSION

TECHNICAL FIELD

The present invention relates to expression vectors containing genes for urea cycle enzymes, animal cells simultaneously transformed with the expression vectors, and the use of the transformed cells in protein over-expression.

PRIOR ART

Most animal cells metabolize amino acids into ammonium ion, carbon dioxide etc. The ammonium ion is utilized in the biosynthesis of proteins, nucleic acids or lipids in which nitrogen is necessary (Ref. Stone and Pitts, J. Clin. Invest. 46, 1141–1150, 1967; and Doyle and Butler, J. Biotechnol. 15, 91–100, 1990). Excess ammonium ion may be toxic and inhibit the cell growth. In animal cell culture, glutamine is used as a major nutrient for the cells. Thus, culture media typically contain a high concentration of glutamine, ranging from 2 to 5 mM (Ref. Reitzer et al., J. Biol. Chem. 254, 2669–2676, 1979; Moreadith and Lehninger, J. Biol. Chem. 259, 6215–6221, 1984; Newland et al., Cytotechnology, 3, 215–229, 1990; and Fitzpatrick et al., Appl. Biochem. Biotechnol. 43, 93–116, 1993). The ammonium ion in the media mostly originates from the metabolism and catabolism of the glutamine (Scheme 1) (Ref. Bray et al., Biochem. J. 44, 625–627, 1949; Tritsh and Moore, Exp. Cell Res. 28, 360–364, 1962; and Ozturk and Palsson, Biotechnol. Prog. 6, 121–128, 1990):

[Scheme 1]

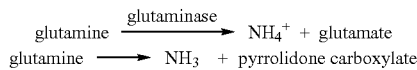

An excess of ammonium ions produced in the reaction presented above is accumulated in the culture media causing cytoxicity and reducing the growth/proliferation rate of the cells (Ref. Bushell et al., Biotechnol. Bioeng. 42, 133–139, 1993).

The mechanism by which ammonium ion causes toxicity is controversial. There are two well-known mechanisms (Ref. MacQueen and Bailey, Bioprocess. Eng. 6, 49–61, 1991): one involves the inhibition of receptor-mediated endocytosis. The weak base $NH_3$ raises intralysosomal pH inhibiting one of the steps of receptor-mediated endocytosis (Ref. King et al., Proc. Natl. Acad. Sci. USA, 77, 3283–3287, 1980; Van Leuven et al., Cell, 20, 37–43, 1980; and Karin and Mintz, J. Biol. Chem. 256, 3245–3252, 1981); and the other involves acidification of the cytoplasm, in which the release of a weak acid, $NH_4^+$ causes the cytoplasm acidification resulting in the inhibition of the cell growth (Ref. Boron and De Weer, J. Gen. Physiol. 67, 91–112, 1976; MacQueen and Bailey, Biotechnol. Bioeng. 35, 897–906, 1990; and MacQueen and Bailey, Bioprocess. Eng. 6, 49–61, 1991).

Whichever mechanism causes the effects of ammonium ion toxicity on animal cells, accumulated ammonium ion can inhibit cell growth (Ref. Eaton et al., Virology, 18, 102–108, 1962; Ryan and Cardin, Proc. Soc. Exp. Biol. Med. 123, 27–30, 1966; Visek et al., J. Cell. Physiol. 80, 373–381, 1972; Butler et al., J. Cell Sci. 61, 351–363, 1983; Butler and Spier, J. Biotechnol. 1, 187–196, 1984; Reuveny et al., J. Immunol. Methods, 86, 53–59, 1986; Dodge et al., Enzyme Microb. Technol. 9, 607–611, 1987; Macmillan, Large Scale Cell Culture Technology, Hanser, N.Y. pp. 21–58, 1987; Hasell et al., Appl. Biochem, Biotechnol. 30, 29–41, 1991; McQueen and Bailey, Bioprocess. Eng. 6, 49–61, 1991; Ozturk et al., Biotechnol. Bioeng. 39, 418–431, 1992; Racher et al., J. Biotechnol. 29, 145–156, 1993; and Ph.D Thesis No. 1412, Ecole Polytechnique Federal de Lausanne (EPFL), Switzerland, 1995) and/or prevent production of intracellular substances (Ref. Eaton and Scala, Virology, 13, 300–307, 1961; Jensen and Liu, Proc. Soc. Exp. Biol. Med. 107, 834–838, 1961; Furusawa and Cutting, Proc. Soc. Exp. Biol. Med. 111, 71–75, 1962; Commoy-Chevalier et al., J. Gen. Virol. 41, 541–547, 1978; Ito and McLimans, Cell Biol. Int. Rep. 5, 661–666, 1981; Reuveny et al., J. Immunol. Methods, 86, 53–59, 1986; Farias et al., Arch. Virol. 98, 155–162, 1988; Doyle and Butler, J. Biotechnol. 15, 91–100, 1990; Atanassov et al., Res. Immunol. 145, 277–288, 1994; Hansen and Emborg, Biotechnol. Prog. 10, 121–124, 1994; Anderson and Goochee, Biotechnol. Bioeng. 47, 96–105, 1995; and Zanghi et al., Biotechnol. Prog. 14, 834–844, 1998).

With the recent rapid progress of the biotechnology, expression and mass production of proteins with physiological activity have been possible in animal cells in culture (Ref. Adams and Schmidli, Can. J. Chem. Eng. 64, 531–539, 1986). However, it is actually impossible to maximize the production of such proteins with physiological activity because of the toxicity of ammonium ions accumulated in the culture medium in the case of mass culture of animal cells. It is well known that ammonium ion decreases the productivity and final activity of proteins through inhibitions of glycosylations occurring at golgi body as well as cell growth (Andersen et al., Biotechnology and Bioengineering 47, 96–105, 1995; Yang et al., Biotechnology Progress 16, 751–759, 2000). Accordingly, many methods for reducing the amount of accumulated ammonium ions have been tried. For example, glutamine is replaced with glutamate or other amino acids (Ref. Darnell and Eagle, Virology, 6, 556–566, 1958; Hassell and Butler, J. Cell Sci. 96, 501–508, 1990; and Kurano et al., J. Biotechnol. 15, 113–128, 1990), or a small amount of glutamine is used (Ref. Glacken et al., Biotechnol. Bioeng. 28, 1376–1389, 1986; Hiller et al., Biotechnol. Bioeng. 44, 303–321, 1994; and Ljunggren and Haggstrom, Biotechnol. Bioeng. 44, 808–818, 1994). Alternatively, a gas-permeable hydrophobic porous membrane has been suggested to remove ammonia or ammonium ions (Ref. Schneider et al., Enzyme Microb. Technol. 16, 957–963, 1994; Capiaumont et al., J. Biotechnol. 39, 49–58, 1995; and Schneider, PhD Thesis No. 1412, Ecole Polytechnique Federal de Lausanne (EPFL), Switzerland, 1995), a nonporous ion-exchange membrane (Ref. Thommes et al., Proceedings of the Eleventh ESACT Meeting, Brighton, UK, pp. 171–175, 1992; and Sikdar and Sawant, Sep. Sci. Technol. 29, 1579–1591, 1994), an ion-exchange resin (Ref. Ito et al., Proceedings of the International Symposium on Growth and Differentiation of Cells in Defined Environment, Fukuoka, Japan, pp. 437–442, 1984; Carbonell et al., Proceeding of the Eleventh ESACT Meeting, Brighton, UK, pp. 166–169, 1992; Jeong and Wang, Biotechnol, Techn. 6, 341–346; Nayve et al., J. Biotechnol. 34, 217–225, 1994; and Capiaumont et al., J. Biotechnol. 39, 49–58, 1995) or electrodialysis (Ref. Chang et al., Biotechnol. Bioeng. 47, 308–318, 1995a; and Chang et al., Biotechnol. Bioeng. 47, 319–326, 1995b). However, the removal of ammonia or ammonium ions using the methods mentioned above is problematic in regard to their limitations and efficiency. For example, the method using an ion-exchange resin makes it difficult to reuse the resin and separate the culture media and the cells from an adsorbent and reduces productivity due to cohesion of the products on the surface of the adsorbent (Ref. Jeong et al., Biotechnol. Bioeng. 11, 329–339, 1996). Recently, expression for antisense RNA of GPI (Glucosamine-6-phosphate isomerase) has been reported to reduce the formation of ammonium ions, which also has a problem in that the GPI expression of antisense clones is unstable due to the inducibility of GPI by its substrate ammonium ion (Ref. Cayli et al., Biotechnol. Bioeng. 65, 192–200, 1999).

As described above, many studies have been continuously made on methods for selectively preventing the accumulation of ammonium ions in animal cells or eliminating the ammonium ions.

Thus the inventors of this invention, directing their attention to the enzymatic system for removing ammonia from organisms, that is, urea cycle, found out that transformation of animal cells with vectors containing a gene for enzymes involved in the urea cycle reduces the ammonia accumulation in the cell culture medium and increases the cell growth rate, leading to the present invention.

DISCLOSURE OF THE INVENTION

It is therefore, an object of the present invention to provide expression vectors containing genes for coding enzymes involving a urea cycle.

It is another object of the present invention to provide animal cells simultaneously transformed with the expression vectors.

It is further object of the present invention to provide a method for using the transformed animal cells in the overexpression of proteins.

BEST MODE FOR CARRYING OUT THE INVENTION

Hereinafter, the present invention will be described in further detail.

The present invention makes use of the principle of the urea cycle in order to reduce the accumulation of ammonium ions in animal cell culture media.

The urea cycle is a metabolic pathway for disposal of toxic metabolite ammonia as a urea in mammals. The urea cycle is catalyzed by five enzymes: carbamoyl phosphate synthetase I (CPS I), ornithine transcarbamoylase (OTC), argininosuccinate synthetase (AS), argininosuccinate lyase (AL) and arginase (Arg). The first two enzymes of the urea cycle are located within the mitochondrial matrix (Ref. Gamble and Lehninger, J. Biol. Chem. 248, 610–618, 1973; and Clark, J. Biol. Chem. 251, 950–161, 1976) and the remaining three enzymes are cytosolic (Ref. Pierson et al., J. Biol. Chem. 252, 6464–6469, 1977). CPS I promotes the formation of carbamoyl phosphate from ammonium ion and carbon dioxide in the first step (Ref. Powers, J. Biol. Chem. 256, 11160–11165, 1981). OTC catalyzes the formation of citrulline from carbamoyl phosphate and ornithine in the second step (Ref. Mori et al., Mol. Cell Biochem. 49, 97–111, 1982; and Sheffield et al., Biochem. Biophys. Res. Commun. 134, 21–28, 1986). AS is involved in the formation of argininosuccinate from citrulline and aspartate in the third step and AL facilitates the formation of arginine and fumarate from argininosuccinate in the fourth step. ARG catalyzes the formation of ornithine and urea from arginine in the fifth step as described in the following scheme (Ref. Meijer et al., Physiological review. 70, 701–748, 1990).

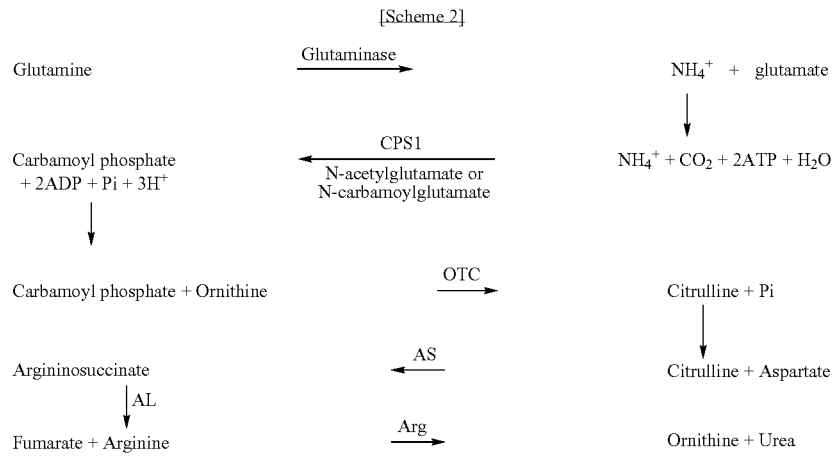

[Scheme 2]

According to the present invention, use is made of a known rat CPS I cDNA sequence (Ref. Nyunoya et al., J. Biol. Chem. 260, 9346–9356, 1985) to synthesize oligonucleotide sequence number 13 and 14, which are then used as primers in PCR to clone rat CPS I full coding cDNA.

Use is also made of a known rat OTC cDNA sequence (GenBank Accession No. K00001) to clone the ORF (Open Reading Frame) region of a rat OTC gene using primer sequence number 3 and 4.

Oligonucleotide sequence number 5 and 6 are synthesized based on the known rat AS cDNA sequence (GenBank Accession No. M36708) and then used to clone the rat AS full coding cDNA.

Figure 1A:
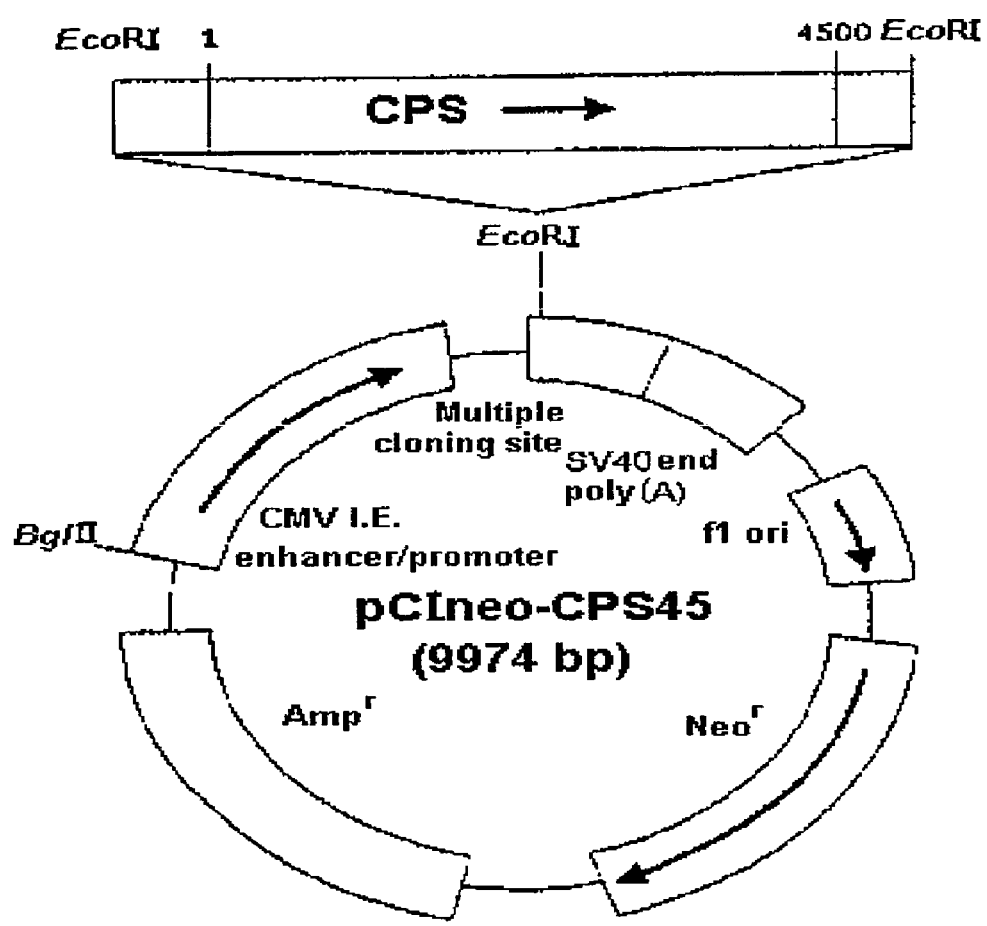
FIG. 1a shows a map of an expression vector pCIneo-CPS45 containing a CPS I gene.
Figure 1B:
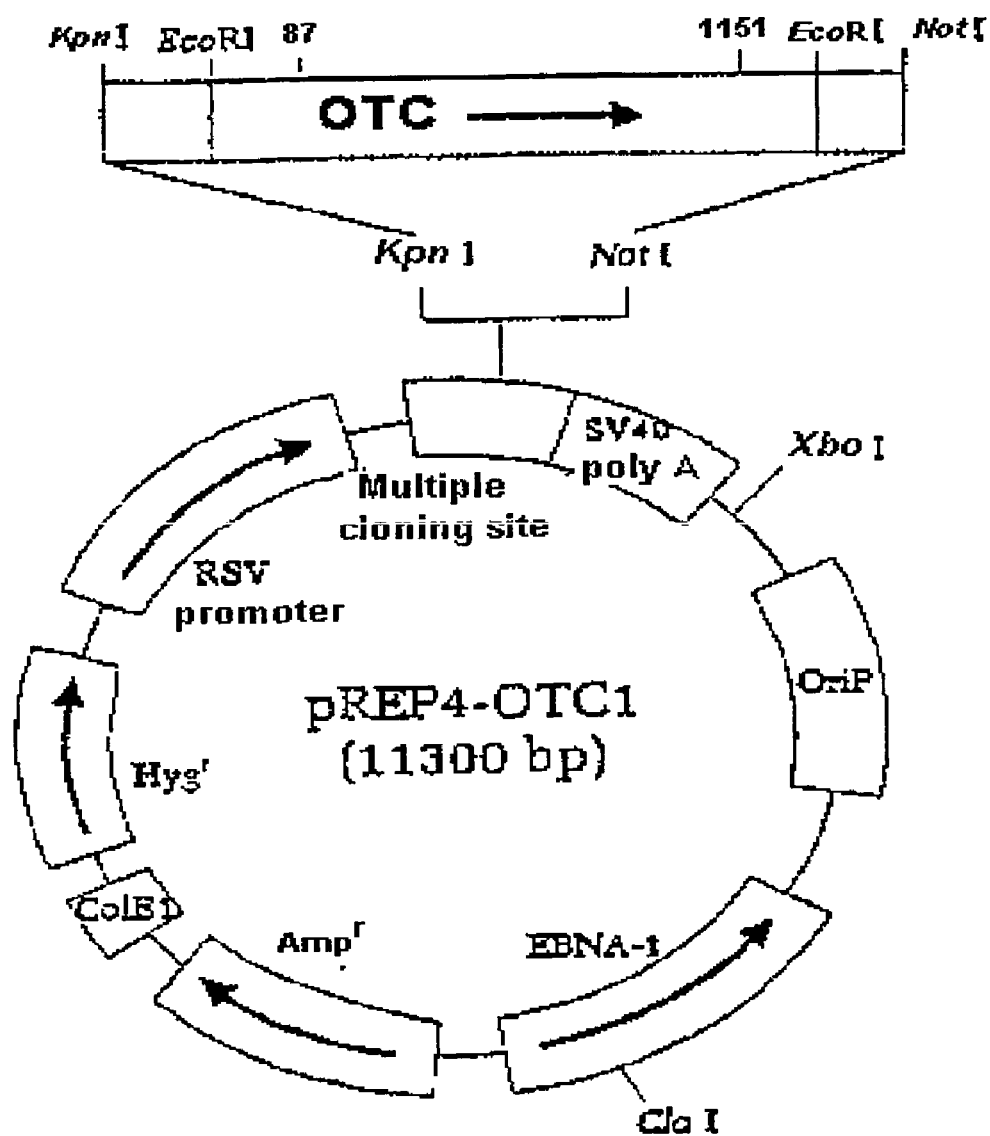
FIG. 1b shows a map of an expression vector pREP4-OTC1 containing an OTC gene.
Figure 1C:
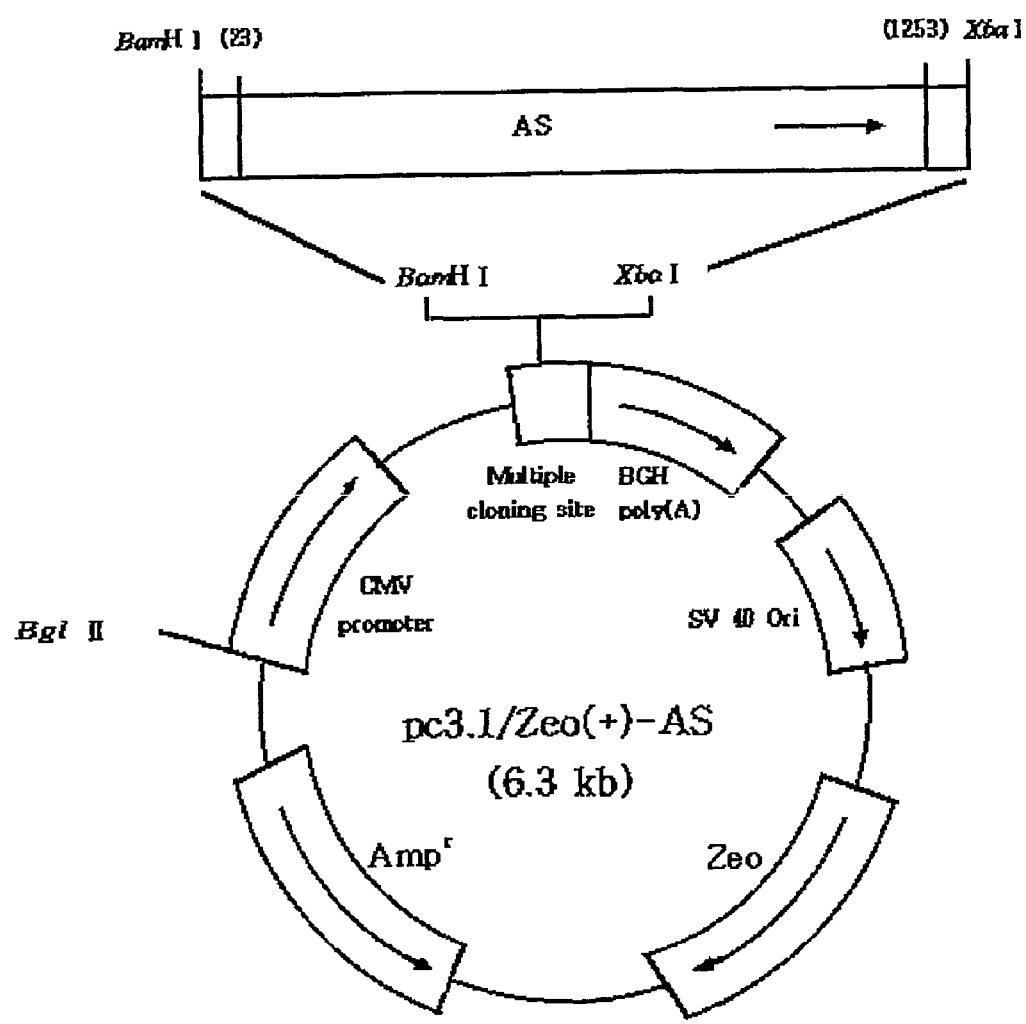
FIG. 1c shows a map of an expression vector pc3.1/Zeo(+)-AS containing an AS gene.
Figure 1D:
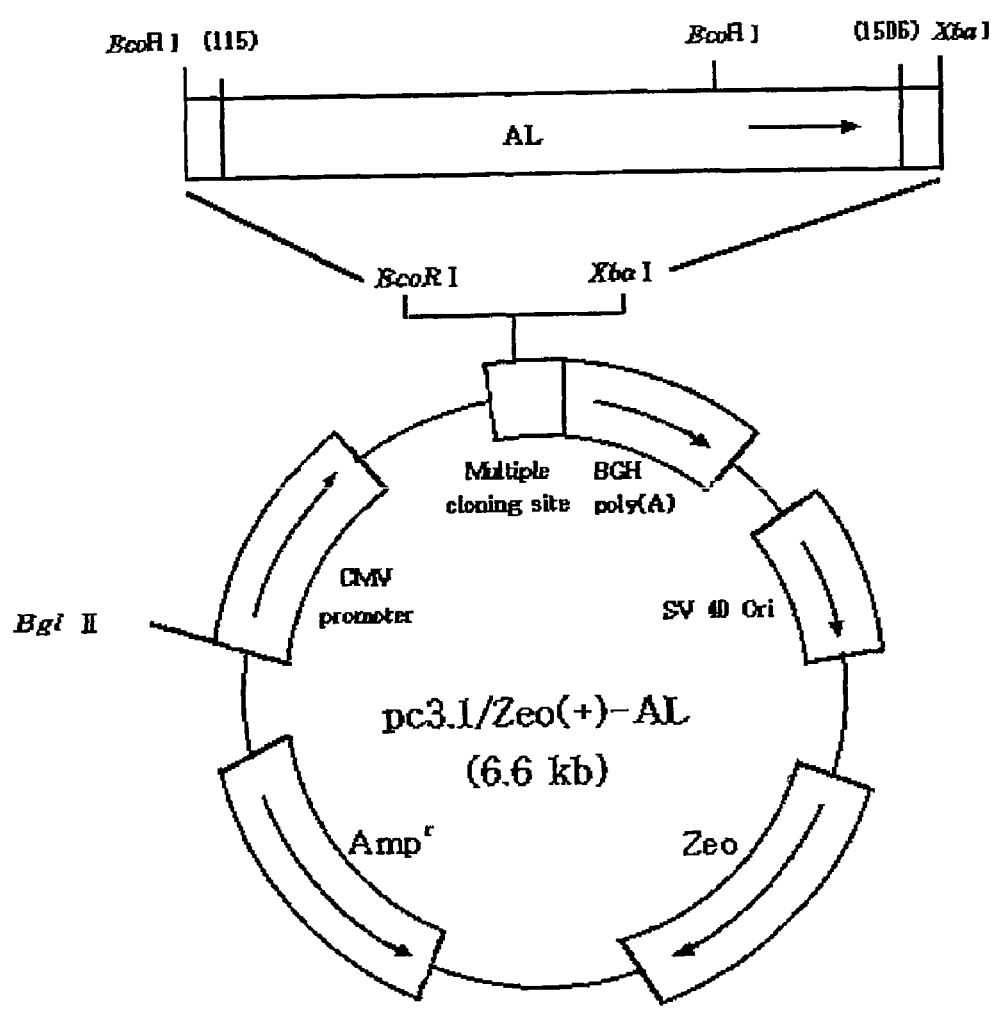
FIG. 1d shows a map of an expression vector pc3.1/Zeo(+)-AL containing an AL gene.
Figure 1E:
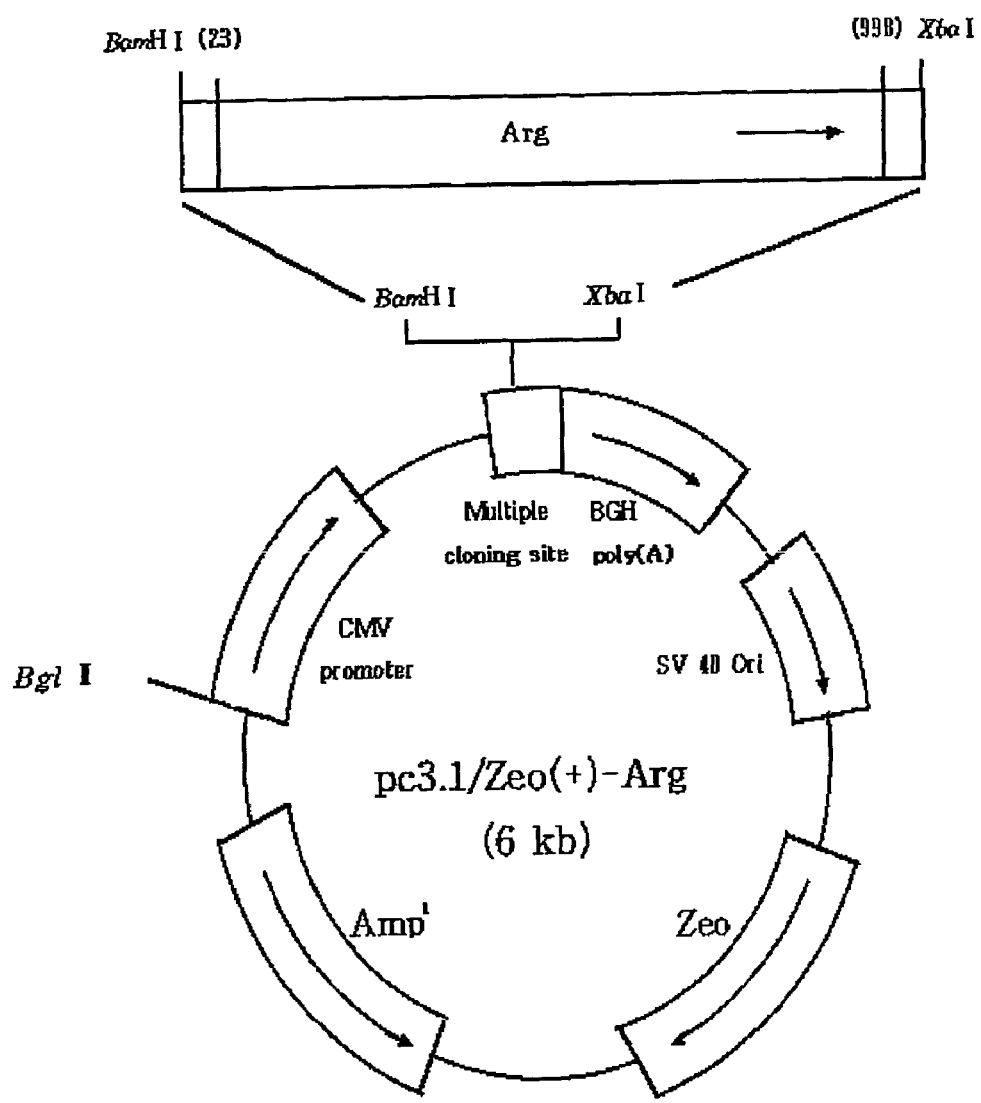
FIG. 1e shows a map of an expression vector pc3.1/Zeo(+)-ARG containing an ARG gene.

Oligonucleotide sequence number 7 and 8 are synthesized based on the rat ARG cDNA sequence (GenBank Accession No. J02720) and then used to clone the rat ARG full coding cDNA. The cloned CPS I and OTC genes are inserted into animal cell expression vectors pCIneo and pREP4 to produce a pCIneo-CPS45 recombinant plasmid (KCTC 0846BP deposited on Aug. 7, 2000) and a pREP4-OTC1 recombinant plasmid (KCTC 0847BP deposited on Aug. 7, 2000), respectively (See FIGS. 1a and 1b). The cloned AS and ARG genes are inserted into an animal cell expression vector pcDNA3.1/Zeo(+) to produce a pc3.1/Zeo(+)-AS recombinant plasmid (KCTC 10014BP deposited on Jul. 12, 2001) and a pc3.1/Zeo(+)-ARG recombinant plasmid (KCTC 10012BP deposited on Jul. 12, 2001), respectively (See FIGS. 1c and 1e). As for the AL gene, a known humane AL gene (Ref. Lambert et al., Molecular and Cellular Biology. 6, 1722–1728, 1986) is inserted into an expression vector pcDNA3.1/Zeo(+) to produce a pc3.1/Zeo(+)-AL recombinant plasmid (KCTC 10013BP deposited on Jul. 12, 2001) (See FIG. 1d). CPS I, OTC, AS, AL and ARG genes may be inserted into the restriction sites of other expression vectors than the above-mentioned vectors pCIneo, pREP4 and pcDNA3.1/Zeo(+). CPS I, OTC, AS, AL and ARG genes from all mammals are available because of high homology among animal genes as shown in Table 1.

TABLE 1

| | Species | Nucleotide Level | | Protein Level | |
|---|---|---|---|---|---|
| | | Accession. No. | Identity (%) | Accession No. | Similarity (%) |
| CPSI | Homo sapiens (Human) | XM_40883 | 89 | XP_010819 | 96 |
| OTC | Mus musculus (Mouse) | NM_008769 | 96 | NP_032795 | 98 |
| | Homo sapiens (Human) | XM_013065 | 90 | AF241726 | 95 |
| | Sus scrofa (Pig) | Y13045 | 87 | Y13045 | 97 |
| | Bos Taurus (Cow) | AF134841 | 87 | AF134841 | 94 |
| AS | Mus musculus (Mouse) | BC002074 | 95 | NP_031520 | 96 |
| | Homo sapiens (Human) | BC009243 | 89 | XP_033324 | 96 |
| | Bovine | M26198 | 88 | P14568 | 96 |
| AL | Rattus norvegicus (Norway Rat) | NM_021577 | 85 | NP_067588 | 93 |
| | Bos Taurus (Cow) | AF156096 | 88 | | |
| Arg | Mus musculus (Mouse) | U51805 | 91 | U51805 | 96 |
| | Homo sapiens (Human) | M14502 | 83 | M14502 | 92 |
| | Oryctolagus cuniculus (Rabbit) | AF365403 | 85 | AF365403 | 92 |

To determine the effect of the CPS I and OTC expressions in animal cells on the formation of ammonium ions, CHO dhfr⁻ cells are transformed with expression vectors pCIneo-CPS45 and pREP4-OTC1.

In order to obtain a CHO cell line expressing CPS I and OTC permanently, the present invention transforms the CHO cell line stably expressing CPS I with an expression vector pREP4-OTC1 containing the OTC gene. The present transformant CHO-OTC1-A19 (CHO/dhfr⁻) obtained by the transformation of CHO/dhfr⁻ (ATCC CRL-9096) with expression vectors pCIneo-CPS45 and pREP4-OTC1 was deposited under No. KCTC 0845BP at Korea Research Institute of Bioscience and Biotechnology on Aug. 7, 2000.

To determine the effect of expression of CPS I, OTC, AS, AL and ARG in CHO cells on the formation of ammonium ions, CHO-OTC1-A19 cells are transformed with pc3.1/Zeo (+)-AS to obtain CHO-AS-16 (KCTC 10031BP deposited on Aug. 6, 2001); with the expression vectors pc3.1/Zeo(+)-AS and pc3.1/Zeo(+)-AL to obtain CHO-AL-19 KCTC 10015BP deposited on Jul. 12, 2001); and with the expression vectors pc3.1/Zeo(+)-AS, pc3.1/Zeo(+)-AL and pc3.1/Zeo(+)-ARG to obtain CHO-ARG-11 (KCTC 10030BP deposited on Aug. 6, 2001), respectively.

Although a calcium phosphate method is used in the transformation, other known methods using lipopectin or the like can be used. The animal cell as used herein for transformation is preferably selected from the group consisting of a CHO (Chinese Hamster Ovary) cell, COS-7 (Monkey, African green) cell, NIH/3T3 (Mouse fibroblast) cell, BHK-21 (Baby Hamster Kidney, Syrian golden) cell, Hela (Human carcinoma) cell, Vero (Monkey kidney, African green) cell and C127 (Mouse) cell. The CHO dhfr⁻ cell is preferred due to its high transfection rate.

Figure 7:
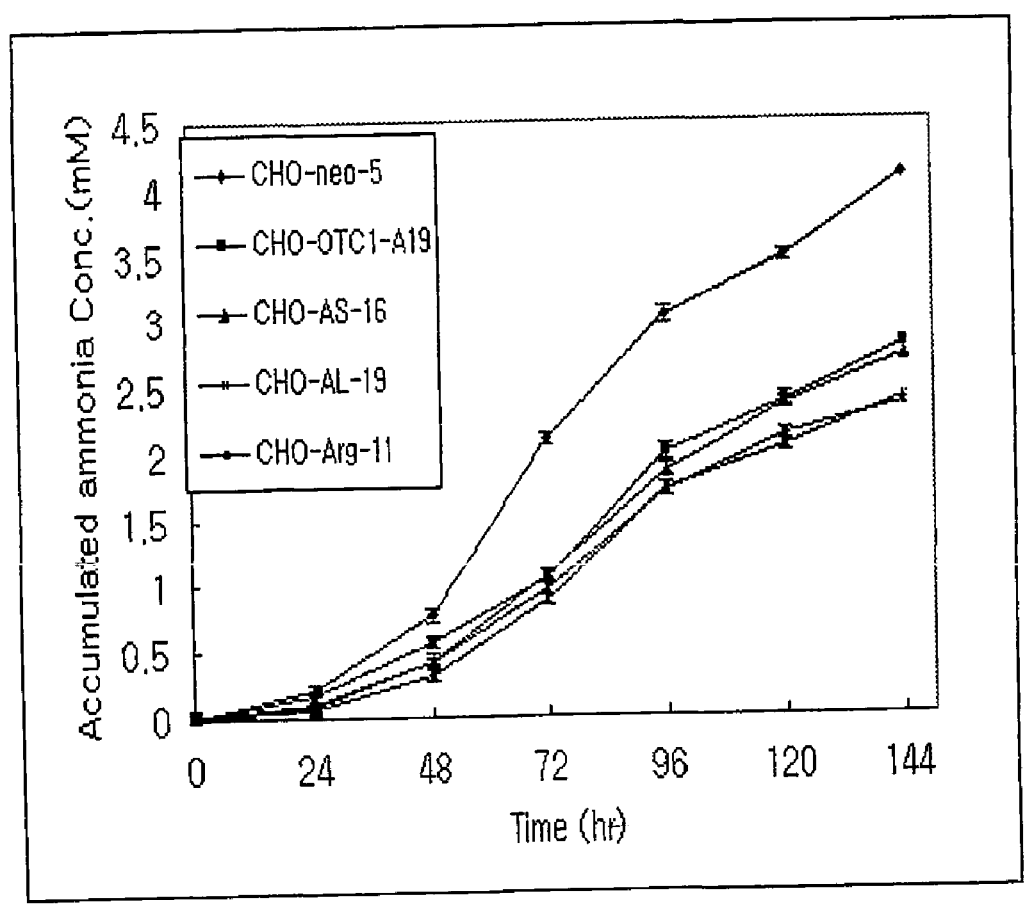
FIG. 7 is a graph showing the ammonia accumulation in the culture media of CHO-neo 5 cell line (control), a CHO-OTC1-A19 cell line simultaneously transformed with expression vectors pCIneo-CPS45 and pREP4-OTC1, a CHO-AS-16 cell line simultaneously transformed with expression vectors pCIneo-CPS45, pREP4-OTC1 and pc3.1/Zeo(+)-AS, a CHO-AL-19 cell line simultaneously transformed with expression vectors pCIneo-CPS45, pREP4-OTC1, pc3.1/Zeo(+)-AS and pc3.1/Zeo(+)-AL, and a CHO-ARG-11 cell line simultaneously transformed with expression vectors pCIneo-CPS45, pREP4-OTC1, pc3.1/Zeo(+)-AS, pc3.1/Zeo(+)-AL and pc3.1/Zeo(+)-ARG.
Figure 8:
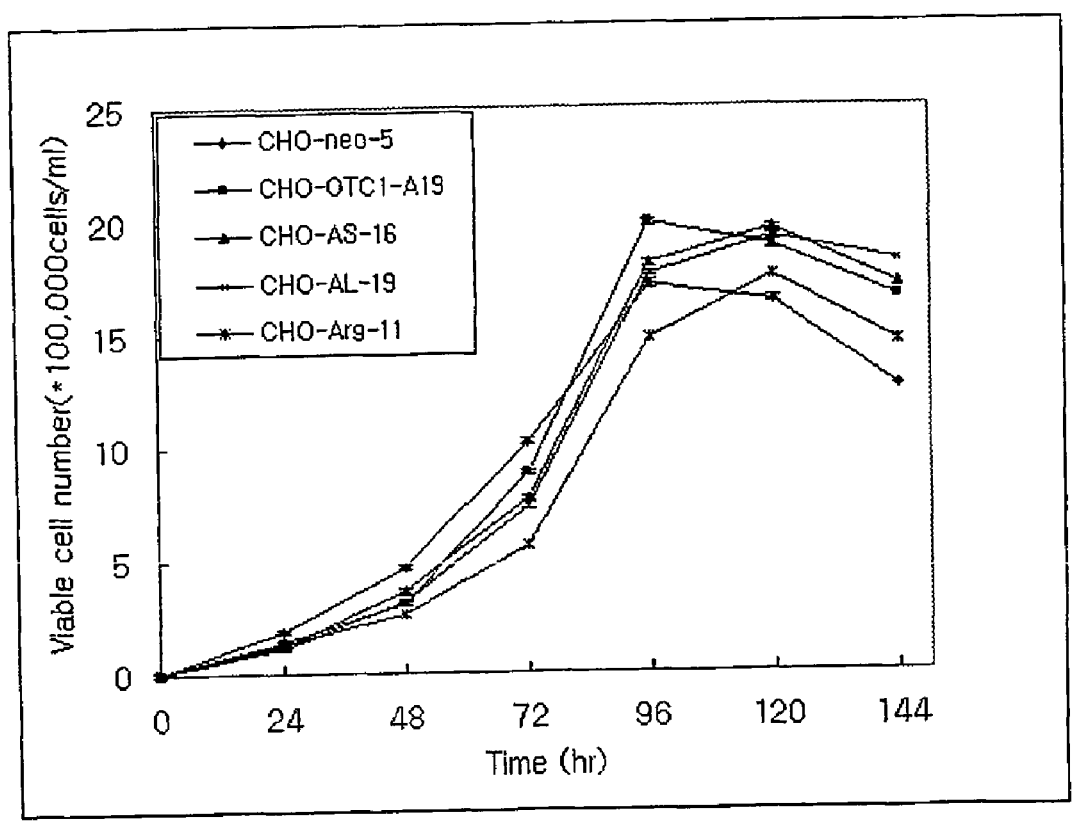
FIG. 8 is a graph showing the growth rate of a CHO-neo-5 cell line (control), a CHO-OTC1-A19 cell line simultaneously transformed with expression vectors pCIneo-CPS45 and pREP4-OTC1, a CHO-AS-16 cell line simultaneously transformed with expression vectors pCIneo-CPS45, pREP4-OTC1 and pc3.1/Zeo(+)-AS and pc3.1/Zeo(+)-AL, and a CHO-ARG-11cell line simultaneously transformed with expression vectors pCIneo-CPS45, pREP4-OTC1, pc3.1/Zeo(+)-AS and pc3.1/Zeo(+)-AL, and a CHO-ARG-11 cell line simultaneously transformed with expression vectors pCIneo-CPS45, pREP4-OTC1, pc3.1/Zeo(+)-AS, pc3.1/Zeo(+)-AL and pc3.1/Zeo(+)-ARG.

A measurement of the accumulation of ammonia in the culture medium and the growth rate of cells for the CHO-OTC1-A19 of the present invention that expresses both CPS I and OTC synthesized as described above shows that the CHO-OTC1-A19 cell line has a lower ammonia accumulation by about 25 to 33% and a higher growth rate by about 15 to 30% than the control, i.e., CHO-neo-5 cell line (See FIGS. 7 and 8).

The accumulation of ammonia in the culture medium and the growth rate of cells are also measured for the CHO-AS-16 cell lien that stably expresses CPS I, OTC and AS, the CHO-AL-19 cell line that stably expresses CPS I, OTC, AS and AL, and the CHO-ARG-11 cell line that stably expresses CPS I, OTC, AS, AL and ARG. The results are then compared with those of the negative control, i.e., CHO-neo-5 and the above-mentioned CHO-OTC1-A19 of the present invention.

The accumulation of ammonia is almost the same in the three cell lines, CHO-AS-16, CHO-AL-19 and CHO-ARG-11. The CHO-AS-16 cell line has a lower accumulation of ammonia than the negative control, CHO-neo-5 by about 30 to 40% and than the CHO-OTC1-A19 cell line by about 2 to 3% after period of 96 hours in the culture. The CHO-AL-19 cell line has a lower accumulation of ammonia than the CHO-neo-5 by over 40% on average and than the CHO-OTC1-A19 by about 15% after period of 96 to 144 hours. The CHO-ARG-11 cell line has a lower accumulation of ammonia than the CHO-neo-5 by about 40 to 50% on average and than the CHO-OTC1-A19 cell line by about 15% (See FIG. 7).

It can be seen that the three cell lines, CHO-AS-16, CHO-AL-19 and CHO-Arg-11 all have higher growth rates than the negative control cell line, CHO-neo-5 by 36%, 44% and 16%, respectively (See FIG. 8).

Figure 9:
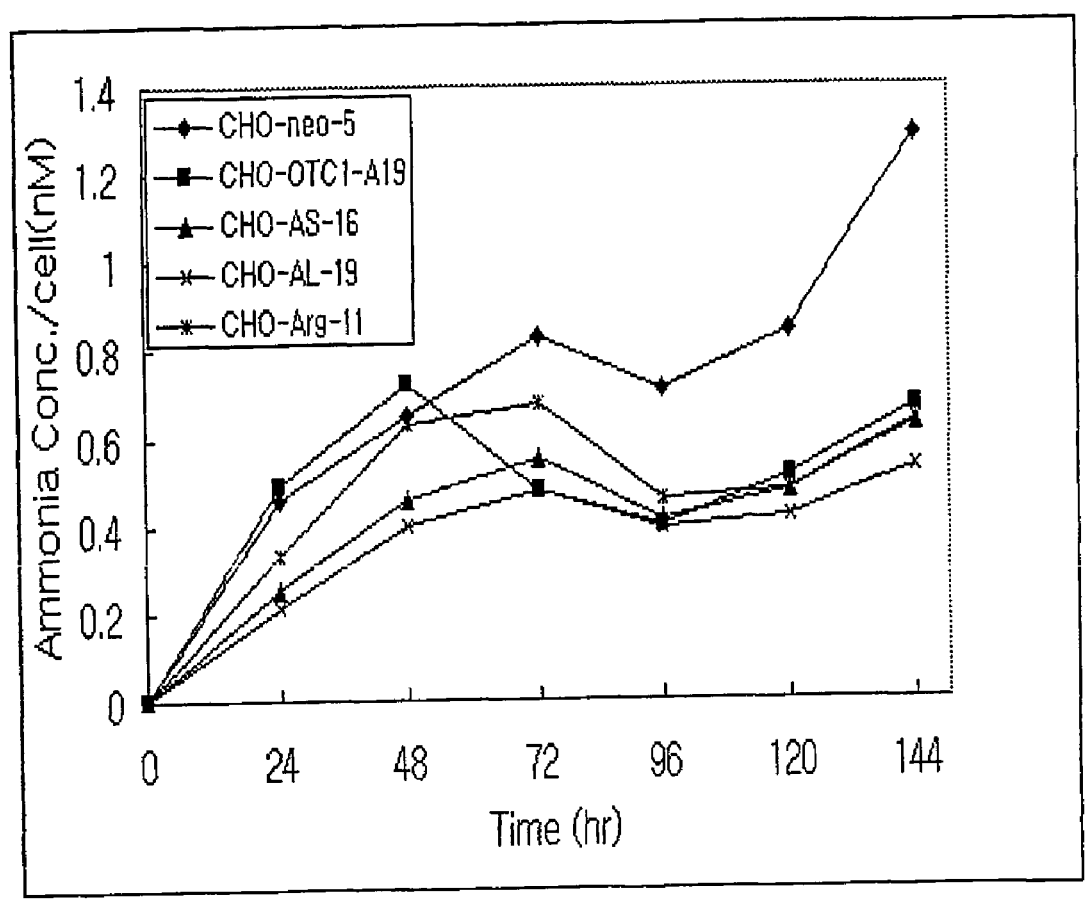
FIG. 9 is a graph showing the ammonia concentration per cell in a culture medium of a CHO-neo-5 cell line (control), a CHO-OTC1-A19 cell line simultaneously transformed with expression vectors pCIneo-CPS45 and pREP4-OTC1, a CHO-AS-16 cell line simultaneously transformed with expression vectors pCIneo-CPS45, pREP4-OTC1 and pc3.1/Zeo(+)-AS, a CHO-AL-19 cell line simultaneously transformed with expression vectors pCIneo-CPS45, pREP4-OTC 1, pc3.1/Zeo(+)-AS and pc3.1/Zeo(+)-AL, and a CHO-ARG-11 cell line simultaneously transformed with expression vectors pCIneo-CPS45, pREP4-OTC1, pc3.1/Zeo(+)-AS, pc3.1/Zeo(+)-AL and pc3.1/Zeo(+)-ARG.

Based on the results shown in FIGS. 7 and 8, the concentration of ammonia per cell in the culture medium can be calculated and is shown in FIG. 9. After a period of 96 hours in a culture at which a high concentration of cells is maintained, the CHO-AS-16 cell line has a lower concentration of ammonia per cell than the CHO-neo-5 by about 40 to 50% and than the CHO-OTC1-A19 cell line by about 6%. The CHO-AL-19 cell line also has a lower concentration of ammonia per cell than the CHO-neo-5 by about 45 to 60% and than the CHO-OTC1-A19 cell line by about 20%. The CHO-Arg-11 cell line has a lower concentration of ammonia per cell than the CHO-neo-5 by about 35 to 50% after 96 hours of culture and than the CHO-OTC1-A19 cell line by about 4 to 6% after 122 to 144 hours.

It is therefore revealed that those animal cells that are transformed with vectors containing CPS I and OTC genes, vectors containing CPS I, OTC and AS genes, vectors containing CPS I, OTC, AS and AL genes, or vectors containing CPS I, OTC, AS, AL and ARG genes have a low accumulation of ammonia in the culture medium as well as a high growth rate of cells and thus are effective in over expression of proteins. Specifically preferred are animal cells, such as CHO-OTC1-A19 (CHO/dhfr) transformed with two expression vectors pCIneo-CPS45 and pREP4-OTC1; CHO-AS-16 (CHO/dhfr) transformed with three expression vectors pCIneo-CPS45, pREP4-OTC1 and pc3.1/Zeo(+)-AS; CHO-AL-19 (CHO/dhfr) transformed with four expression vectors pCIneo-CPS45, pREP4-OTC1, pc3.1/Zeo(+)-AS and pc3.1/Zeo(+)-AL; and CHO-ARG-11 (CHO/dhfr) transformed with five expression vectors pCIneo-CPS45, pREP4-OTC1, pc3.1/Zeo(+)-AS, pc3.1/Zeo(+)-AL and pc3.1/Zeo(+)-ARG.

The animal cell transformed with four enzyme genes (i.e., CPS I, OTC, AS and AL) participating in the urea cycle is preferable to the animal cells transformed with two enzyme genes (CPS I and OTC), three enzyme genes (CPS I, OTC and AS) or five enzyme genes (CPS I, OTC, AS, AL and ARG) in regard to low accumulation of ammonia and the high growth rate of cells. Nevertheless, those animal cells transformed with two, three or five enzyme genes of the urea cycle are also effective in reducing the accumulation of ammonia and enhancing the growth rate of cells as can be commercialized.

A better understanding of the present invention may be obtained in light of the following examples which are set forth to illustrate, but are not to be construed to limit the present invention.

In all the following examples, the cloning of all recombinant plasmids was performed in accordance with standard protocol of Sambrook (Ref. Sambrook et al., Molecular Cloning, 1989). The DNA fragment used for insertion of the following DNA was gel-purified by DNA isolation kit (supplied by Bio-Rad Laboratories, Canada). The total RNA was extracted from rat liver with high pure RNA isolation kit (supplied by Boheringer Mannheim, U.S.A.) by the same method in all the following examples.

EXAMPLE 1

Preparation of CPS I Expression Plasmid

In order to prepare CPS I expression plasmid, a full coding region of CPS I cDNA was cloned by the method of RT-PCR. To perform RT-PCR, use was made of total RNA from rat liver with a forward primer having a sequence number 13 and a backward primer having a sequence number 14. With a Titan™ one-tube RT-PCR system (supplied by Boehringer Mannheim, Germany) according to the protocol specified by the manufacturer, the RT reaction was performed in a Personal cycler (supplied by Biometra, Germany) at 50° C. for 30 minutes. After incubation at 94° C. for 2 minutes, the reaction mixture was kept at 94° C. for 30 seconds, at 49° C. for 30 seconds and at 72° C. for 1 minute, which cycle was repeated thirty times. Finally, the RT-PCR mixture was kept at 72° C. for 7 minutes and subjected to electrophoresis on a 0.9% agarose gel. RT-PCR product about 4.5 kb in size was identified by the staining gels with ethidium bromide (EtBr). The DNA fragment was purified and inserted into a pCR2.1 vector (supplied by Invitrogen Co., U.S.A.) using a TA cloning kit (supplied by Invitrogen Co., U.S.A.). The resulting plasmid was named as pCR2.1-CPS45. Subsequently, the pCR2.1-CPS45 plasmid was fragmented with EcoRI and ScaI to obtain a CPS I fragment (Ref. Nyunoya et al., J. Biol. Chem. 260, 9346–9356, 1985). The CPSI fragment was then inserted into a pCIneo vector (supplied by Promega Co., U.S.A.), fragmented with EcoRI, thereby completing a pCIneo-CPS45 recombinant plasmid (See FIG. 1a).

EXAMPLE 2

Preparation of OTC Expression Plasmid

To prepare OTC expression plasmid, RT-PCR was performed in the same manner as described in Example 1, except that use was made with a forward primer having a sequence number 3 and a backward primer having a sequence number 4. After carrying out RT reaction at 50° C. for 30 minutes, PCR was performed with 35 time repetitions of a cycle consisting of 30 second incubation at 94° C., 30 second incubation at 56° C. and at 45 second incubation at 72° C. As a result, DNA about 1064 bp in length was obtained. The DNA was inserted into a pCR2.1 vector (supplied by Invitrogen Co., U.S.A.) using a TA cloning kit (supplied by Invitrogen Co., U.S.A.) to prepare a pCR2.1-OTC1 plasmid. Subsequently, the pCR2.1-OTC1 plasmid was fragmented with an EcoRI enzyme to obtain an OTC fragment. The OTC fragment was then inserted into a pcDNA3.1(+) vector (supplied by Invitrogen Co., U.S.A.) to complete a pcDNA(+)-OTC1 recombinant plasmid.

The pcDNA(+)-OTC1 recombinant plasmid was digested with NotI and then partially digested with KpnI to obtain an ORF (Open Reading Frame) fragment (GenBank Accession No. K00001) of the OTC gene. Fragments containing OTC gene were then inserted into a pREP4 vector (supplied by Invitrogen Co., U.S.A.) to complete a pREP4-OTC1 recombinant plasmid (See FIG. 1b).

EXAMPLE 3

Preparation of AS Expression Plasmid

A full coding region of AS cDNA was cloned by using the RT-PCR method. For RT-PCR, use was made of a total RNA from a rat liver, with a forward primer having a sequence number 5 and a backward primer having a sequence number 6 that were based upon the rat AS cDNA (Ref. Serh et al., Nucleic Acids Res. 16, 9352–9352, 1990). RT-PCR was performed with a One-step RT-PCR kit-AMV (supplied by Takara Co., Japan). RT reaction was carried out at 50° C. for 30 minutes and then PCR was performed. After incubating at 94° C. for 2 minutes, 30 cycles of PCR were performed. The cycle was consisted of incubation at 94° C. for 30 seconds, at 49° C. for 30 seconds and at 72° C. for 45 seconds. RT-PCR product about 1200 bp was identified by an agarose gel electrophoresis. This PCR product was inserted between the CMV promotor of a pcDNA3.1 (+)/V5/His-TOPO vector (supplied by Invitrogen Co., U.S.A.) and a BGH (Bovine Browth Hormone) polyadenylation signal (A) through the TA cloning method using a TOPO TA cloning kit (supplied by Invitrogen Co., U.S.A.). The resulting plasmid was named as a pcDNA3.1 (+)-AS. Subsequently, the pcDNA3.1(+)-AS plasmid was fragmented with BamHI and XbaI enzymes to obtain AS cDNA which was then inserted into the BamHI and XhaI-digested pcDNA3.1/Zeo(+), leading to a completion of a pc3.1/Zeo(+)-AS vector (See FIG. 1c). The plasmid contained a CMV promotor at the 5' side of the AS cDNA and a BGH polyadenylation signal (A) at the 3' side.

The nucleotide sequence of AS cDNA in the pc3.1/Zeo (+)-AS vector was determined by the Sanger dideoxy termination method using an automatic DNA sequencer and then compared to the rat AS cDNA sequence registered in the GenBank (Accession No. M36708). The comparison showed that the nucleotide sequence of the cloned AS cDNA in pc3.1/Zeo(+)-AS is identical to the rat AS cDNA sequence in GenBank.

EXAMPLE 4

Preparation of AL Expression Plasmid

To construct a AL expression vector (pc3.1/Zeo(+)-AL), a pUC19-AL vector containing a human AL cDNA of about 1400 bp (Ref. Dr. Roderick R Mcinnes, The Hospital for Sick Children Research Institute) was digested with XbaI and then partially with EcoRI, resulting in the separation of about 1.6 kb fragment of AL full coding cDNA. A pcDNA3.1/Zeo(+) vector (supplied by Promega Co., U.S.A.) was also digested with the same enzymes. The 1.6 kb cDNA fragment were inserted between a CMV enhancer-promotor and a BGH polyadenylation signal of pcDNA3.1/Zeo(+) to obtain an AL expression vector pc3.1/Zeo(+)-AL (See FIG. 1d).

EXAMPLE 5

Preparation of ARG Expression Plasmid

A full coding cDNA of rat ARG was cloned by the RT-PCR method. For the performance of RT-PCR, use was made of total RNA isolated from rat liver, with a forward primer having a sequence number 7 and a backward primer having a sequence number 8 that were based upon the rat ARG cDNA sequence published previousely (Ref. Kawamoto et al., The Journal of Biological Chemistry, 262, 6280–6283, 1987). RT-PCR was performed with a one-step RT PCR kit-AMV (supplied by Takara Co., Japan). RT reaction was carried out at 50° C. for 30 minutes. After incubating at 94° C. for 2 minutes, PCR was performed with 30 time repetitions of a cycle consisting of 30 second incubation at 94° C., 30 second incubation at 49° C. and at 45 second at 72° C. PCR products were further incubated at 72° C. for 7 minutes for the final trimming. RT-PCR product of about 1000 bp was inserted between the CMV promotor of a pcDNA3.1/V5/His-TOPO vector and a BGH polyadenylation signal (A) through the TA cloning method using a Eucaryotic TOPO TA cloning kit (supplied by Invitrogen Co., U.S.A.) to obtain a pcDNA3.1(+)-ARG recombinant plasmid. Subsequently, the pcDNA3.1(+)-ARG plasmid was fragmented with BamHI and XbaI restriction enzymes and the resulting 1 kb fragment was inserted into BamHI and XbaI-digested pcDNA3.1/Zeo(+) vector containing a zeocin resistance gene. The resulting plasmid was named as pc3.1/Zeo(+)-ARG (See FIG. 1e).

The nucleotide sequence of ARG cDNA in the pc3.1/Zeo(+)-ARG vector was determined by the Sanger dideoxy sequencing method using an automatic DNA sequencer and compared to the rate ARG sequence registered in the GenBank (Accession No. J02720). The comparison showed that two nucleotide sequences were identical.

EXAMPLE 6

Cell Culture and Transformation

CHO dhfr⁻ cells from the ATCC (American Type Culture Collection) were maintained in the MEM-α (Minimum Essential Medium Alpha) medium (supplied by Gibco BRL Products Co., U.S.A.) containing 10% FBS (Fetal Bovine Serum) (supplied by Gibco BRL Products Co., U.S.A.), HT solution (containing 0.1 mM sodium hypoxanthine and 0.016 mM thymine) (supplied by Gibco BRL Products Co., U.S.A.), 1% penicillin-streptomycin (containing 10,000 U/ml penicillin G sodium and 10,000 µg/ml streptomycin sulfate in 0.85% saline water) (supplied by Gibco BRL Products Co., U.S.A.) and 25 mM HEPES (N-2-hydroxyethylpiperazine-N'-2-ethanesulfonic acid).

Transfections were performed by the calcium phosphate co-precipitation method (Ref. Sambrook et al., Molecular Cloning, 1989). For transfections, cells were inoculated at a density of $7 \times 10^5$ cells per 60 mm plate and incubated for 12 hours in a 37° C., 5% $CO_2$ incubator. Each plasmid was linearized by the digestion with BglII to enhance transfection efficiency. Digestion mixture was then extracted with phenol-chloroform and then DNA was precipitated with ethanol followed by the resuspension with $H_2O$ in a concentration of 10 µg/100 µl. Three µl of chloroform was added to the 10 µg/100 µl DNA solution, which was then kept at room temperature for one hour and mixed with 125 µl of 2× HEPES buffer (pH 7.5) and 25 µl of 1.25 M $CaCl_2$ through vortexing every 10 minutes. After being kept at the room temperature for 30 minutes, DNA mixture was added to the prepared cells. The cells were cultured in the growth medium in 5% $CO_2$ incubator at 37° C. for 7 hours. Following a shock with the addition of 15% glycerol diluted with 1× HEPES (pH 7.05) for 2 minutes, cells were washed with PBS twice and placed in the growth medium. After 48 hours, the cells were diluted at a 1:15 ratio and maintained in the media containing an appropriate selection marker to select positive clones. The medium was replaced every four days until the selection of transfectants.

EXAMPLE 7

Expression of CPS I in CHO Cell

CHO dhfr⁻ cells transfected with pCIneo-CPS45 as described in Example 6 was selected in the medium containing G418 (500 µg/ml). RT-PCR was performed to determine the degree of expression of the CPS I gene in the transfectants.

The total RNA was prepared from rat liver using an SNAP™ total RNA isolation kit (supplied by Invitrogen Co., U.S.A.). CHO cells were harvested and dissolved with a Nonidet P40-dissolved buffer and the cytoplasmic RNA was extracted using a high pure RNA isolation kit (supplied by Boheringer Mannheim, Germany) (Ref. Frederick et al., Current Protocols in Molecular Biology Wiley, New York, 1997). The RNA concentration was measured with a spectroscope (supplied by Pharmacia Biotech). RT-PCR was performed with 1 µg of extracted RNA and a forward primer having a sequence number 1 and a backward primer having a sequence number 2 in the same mammer as described in Example 1.

Figure 2:
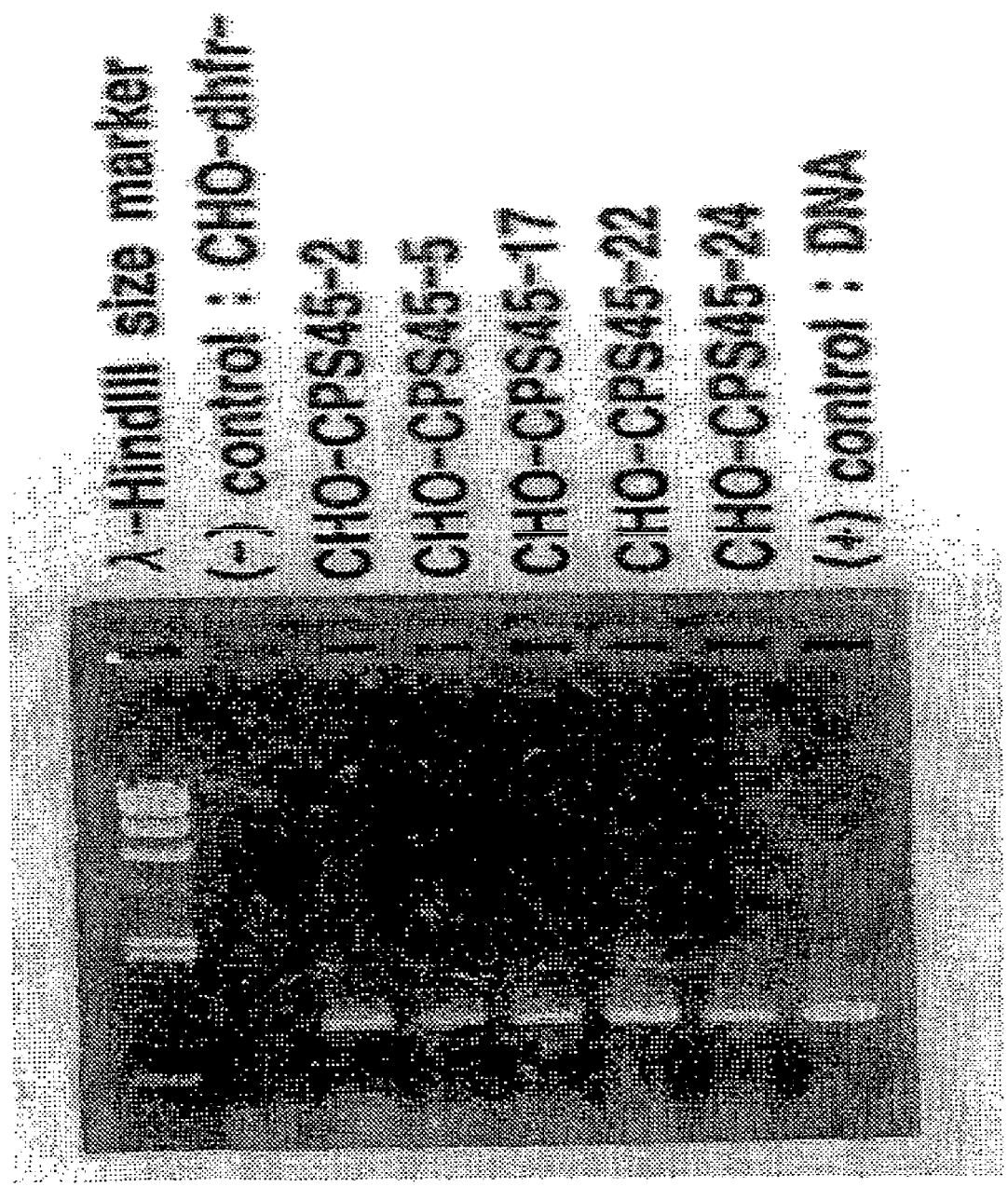
FIG. 2 is a photograph of an agarose gel showing the expression of CPS I mRNA in a CHO cell transformed with an expression vector pCIneo-CPS45.

Each clone has a different level of expression and the CHO-CPS45-22 clone showed the highest expression level of the CPS 1 gene (See FIG. 2). The control was the CHO-neo-5 cell line transformed with the pCIneo vector containing a neomycin resistance gene. The expression level of the neomycin resistance gene was measured in the same manner as described above, which revealed that the neomycin marker gene had a very high expression level.

EXAMPLE 8

Co-Expression of CPS I and OTC in CHO Cells

Figure 3A:
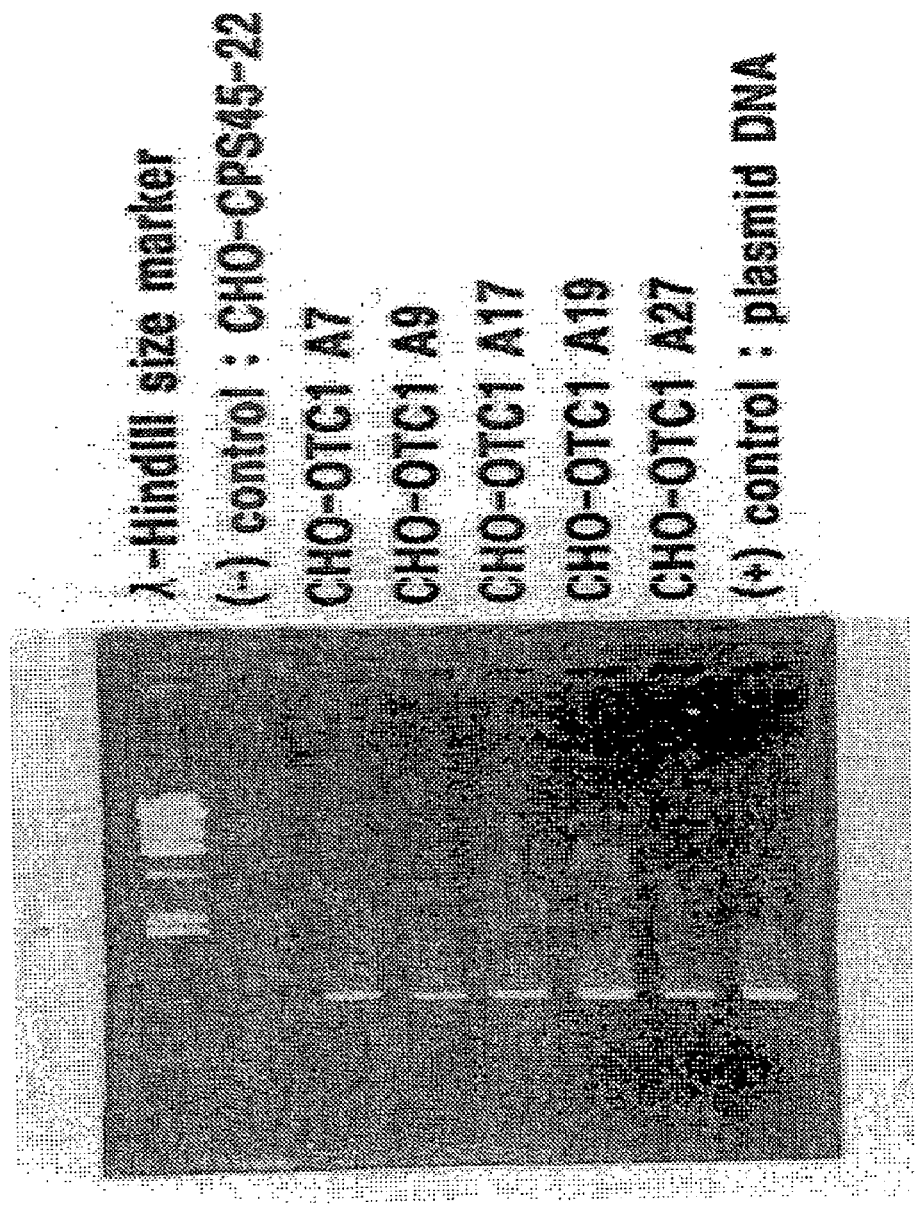
FIG. 3a is a photograph of an agarose gel showing the expression of OTC mRNA in a CHO cell transformed with expression vectors pCIneo-CPS45 and pREP4-OTC1.

To prepare a cell line expressing both CPS I and OTC, CHO-CPS45-22 cells having a high expression level of the CPS I gene were used as the parental cell line. pREP4-OTC1 containing both OTC and hygromycin resistance marker genes was used in the transfection of CHO-CPS45-22 cell with the same manner as described in Example 6. Transfectants were selected in the medium containing hygromycin B. To determine the expression level of OTC gene, total RNA was isolated from the each transfectant and then RT-PCR was performed in the same manner as described in Example 7. Each clone showed a different expression level of OTC mRNA and CHO-OTC1-A19 showed the highest expression level of OTC mRNA (See FIG. 3a).

Figure 3B:
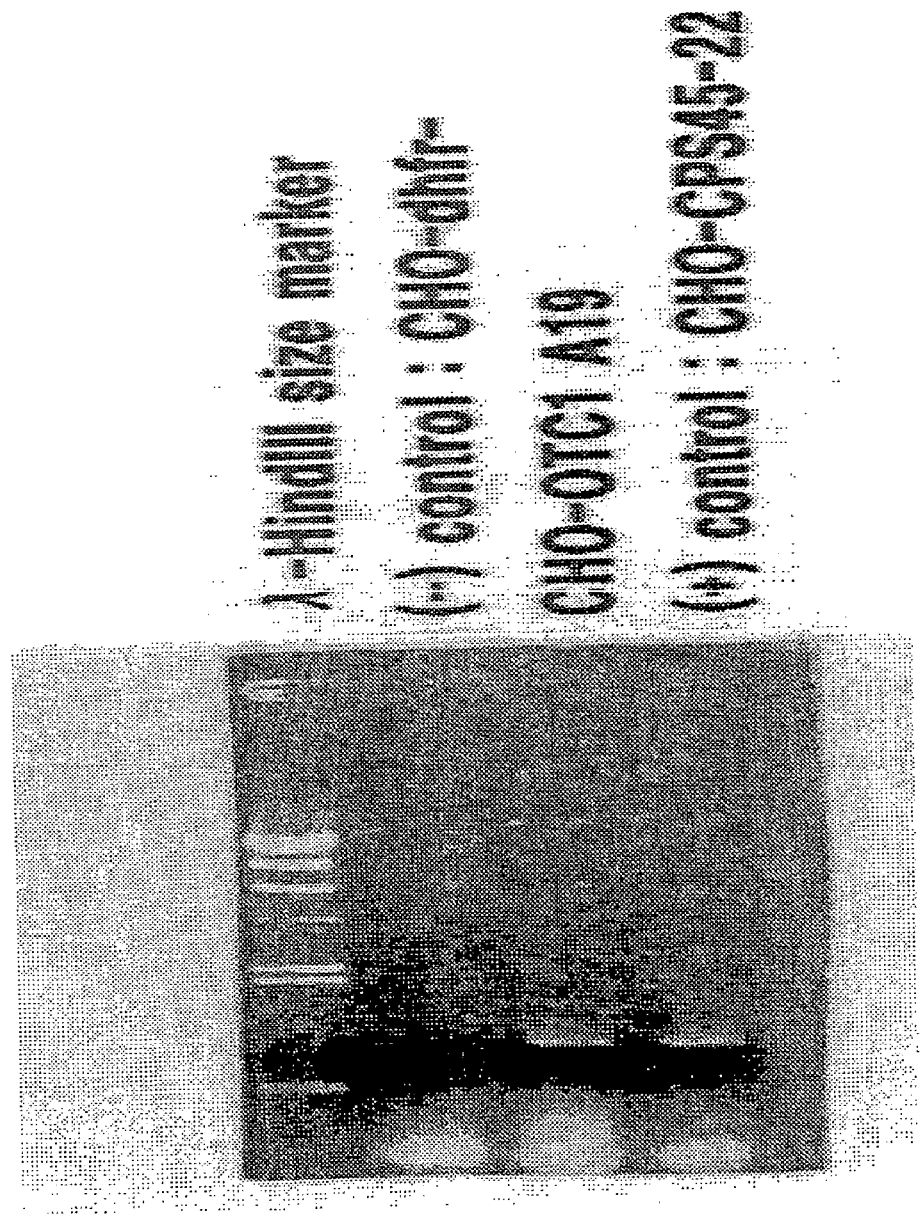
FIG. 3b is a photograph of an agarose gel showing the expression of CPS I mRNA in a CHO cell transformed with expression vectors pCIneo-CPS45 and pREP4-OTC1.

Subsequently, it was determined whether the CPS I was expressed in the OTC-transfected cell line (CHO-OTC1-A19). The expression level of the CPS I gene in the CHO-OTC1-A19 cell was estimated in the same manner as described in Example 7 in regard to the CHO-CPS45-22 cell. It was shown that the CPS I gene is also expressed in the CHO-OTC1-A19 cell line (See FIG. 3b).

EXAMPLE 9

Co-Expressions of CPS I, OTC and AS; CPS I, OTC, AS and AL; and CPS I, OTC, AS, AL and ARG in CHO Cell CHO-OTC1-A19 cells were used in the transfections with the same manner as described in Example 6. DNA was linearized by the digestion with BglII and then used in transfections. Each 10 μg/100 μl DNA solution was added to CHO-OTC1-A19 cells. For example, a 10 μg/100 μl DNA solution containing 10 μg of pc3.1/Zeo(+)-AS was used to prepare a cell line simultaneously expressing CPS I, OTC and AS genes; a 10 μg/100 μl DNA solution containing 5 μg of pc3.1/Zeo(+)-AS and 5 μg of pc3.1/Zeo(+)-AL was added to prepare a cell line simultaneously expressing CPS I, OTC, AS and AL genes; and a 10 μg/100 μl DNA solution containing 3.3 μg of pc3.1/Zeo(+)-AS, 3.3 μg of pc3.1/Zeo(+)-AS and 3.3 μg of pc3.1/Zeo(+)-ARG was added to prepare a cell line simultaneously expressing CPS I, OTC, AS, AL and ARG genes. The DNA solutions were pretreated in the same manner as described in Example 6 and added to the CHO-OTC1-A19 prepared in Example 8 to obtain the respective transfectants. Transfections were performed in the same manner as described in Example 6, except that transfectant selections were carried out with 600 μg/ml zeocin.

EXAMPLE 10

Determination of Simultaneous Expression of CPS I, OTC, AS, AL and ARG in CHO Cells Twenty four colonies were selected from each transfection and propagated into cell lines. RT-PCR was performed to determine if the urea cycle genes introduced in CHO cells were expressed in the established cell lines. Total RNA extracted from the CHO-neo-5 was used as a negative control. pc3.1/Zeo(+)-AL plasmid was served as a positive control for the determination of AL expression and the total RNA extracted from the rat liver for the other four enzymes.

RT-PCR was carried out with 100 ng of total RNA by using One-step RNA PCR kit-AMV (supplied by Takara Co., Japan). For the determination of CPS I mRNA expression, a forward primer of sequence number 1 and a backward primer of sequence number 2 were used. RT reaction was performed at 50° C. for 30 minutes. Then PCR was performed with the 30 time repetitions of the cycle consisting of 3 reactions; 30 second incubation at 94° C., 30 second incubation at 59° C. and 1 minute incubation at 72° C. PCR products were subjected to a further incubation at 72° C. for 7 minutes for the final trimming. For the determination of OTC mRNA expression, RT-PCR was performed using a forward primer of sequence number 3 and a backward primer of sequence number 4 with the 30 time repetitions of the cycle consisting of 3 reactions; 30 second incubation at 94° C., 30 second incubation at 49° C. and 1 minute incubation at 72° C. For the determination of AS, AL and ARG mRNA expressions, RT-PCR was performed in the same manner as described above, except that a forward primer of sequence number 9 and a backward primer of sequence number 10 were used for AS; a forward primer of sequence number 11 and a backward primer of sequence number 12 were used for the determination of AL mRNA expression; and a forward primer of sequence number 7 and a backward primer of sequence number 8 were used for the determination of ARG mRNA.

Figure 4:
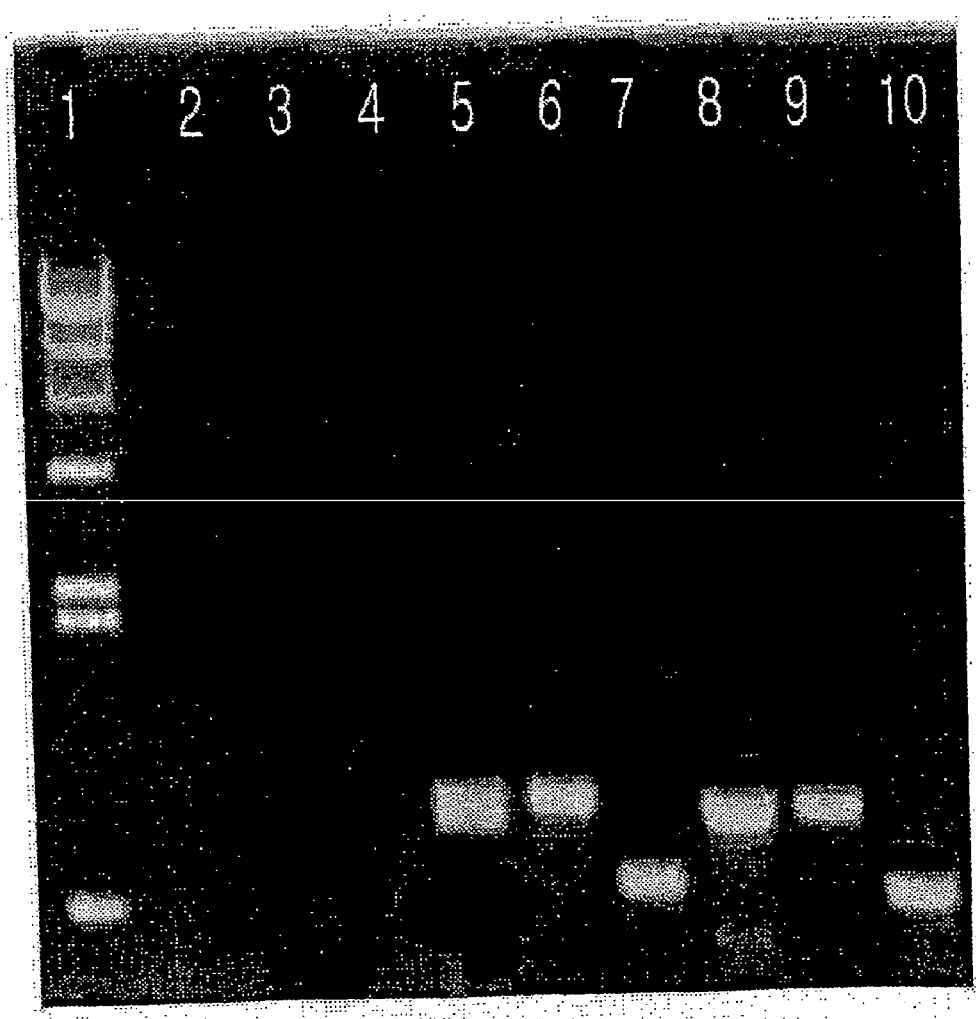
FIG. 4 is a photograph of an agarose gel showing the expression of mRNA for CPS I, OTC and AS genes in a CHO-AS-16 cell line transformed with expression vectors pCIneo-CPS45, pREP4-OTC1 and pc3.1/Zeo(+)-AS, in which lane 1 represents lambda phage DNA fragments digested with HindIII (restriction enzyme) as a size marker; lanes 2, 3 and 4 represent RT-PCR amplified products using a total RNA extracted from a CHO-neo-5 cell line and primers for CPS I (lane 2), for OTC (lane 3) or for AS (lane 4); lanes 5, 6 and 7 represent the RT-PCR amplified products of CPS I, OTC and AS mRNAs using a total RNA extracted from a CHO-AS-16 cell line, respectively; and lanes 8, 9 and 10 represent the RT-PCR amplified products of CPS I, OTC and AS mRNAs using a total RNA extracted from a rat liver cell, respectively.
Figure 5:
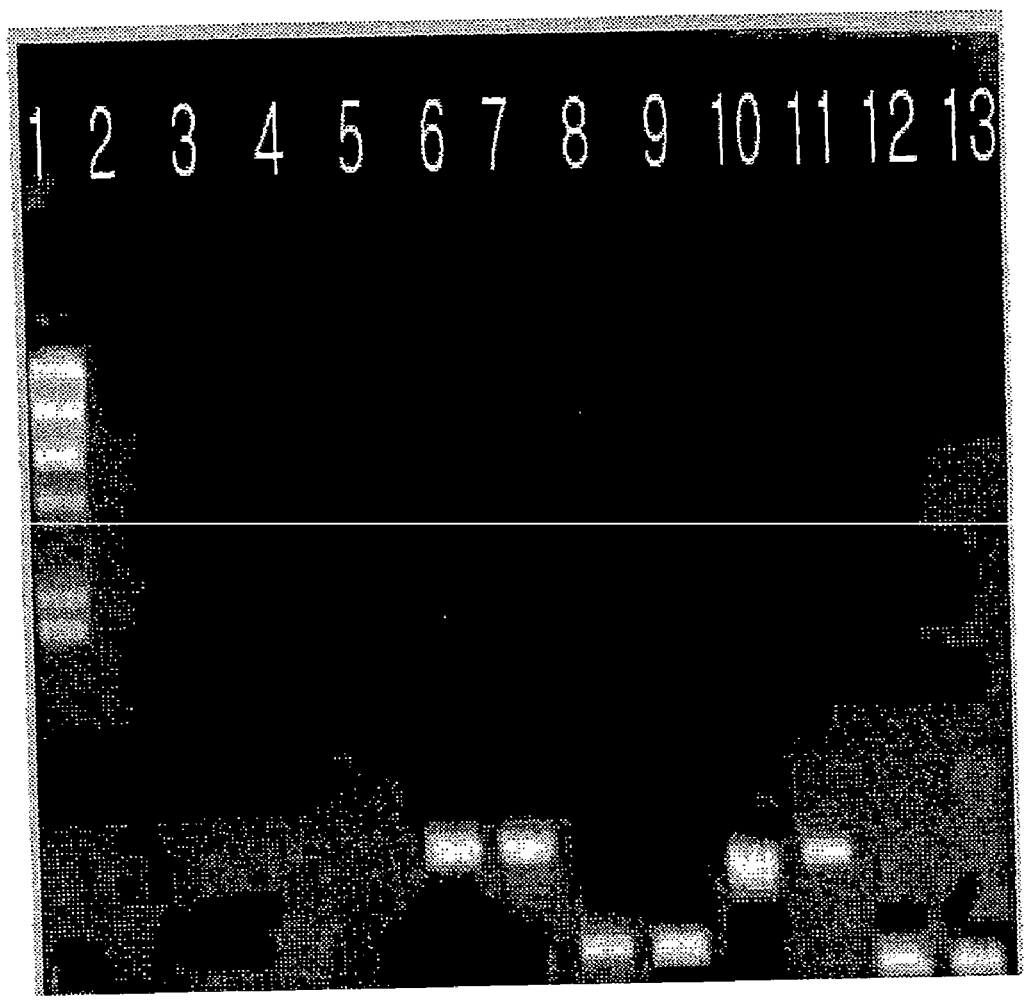
FIG. 5 is a photograph of an agarose gel showing the expression of mRNA for CPS I, OTC, AS and AL genes in a CHO-AL-19 cell line simultaneousely transformed with expression vectors pCIneo-CPS45, pREP4-OTC1, pc3.1/Zeo(+)-AS and pc3.1/Zeo(+)-AL, in which lane 1 represents lambda phage DNA fragments digested with HindIII (restriction enzyme) as a size marker; lanes 2 to 5 represent the RT-PCR amplified products using a total RNA extracted from a CHO-neo-5 cell line and primers for CPS I (lane 2), OTC (lane 3), AS (lane 4) or AL (lane 5); lanes 6 to 9 represent the RT-PCR amplified products of CPS I, OTC, AS and AL mRNAs using a total RNA extracted from a CHO-AS-19 cell line, respectively; lanes 10, 11 and 12 represent the RT-PCR amplified products of CPS I, OTC and AS mRNAs using a total RNA extracted from rat liver, respectively; and lane 13 represents PCR products using pc3.1/Zeo(+)-AL and AL primers.
Figure 6:
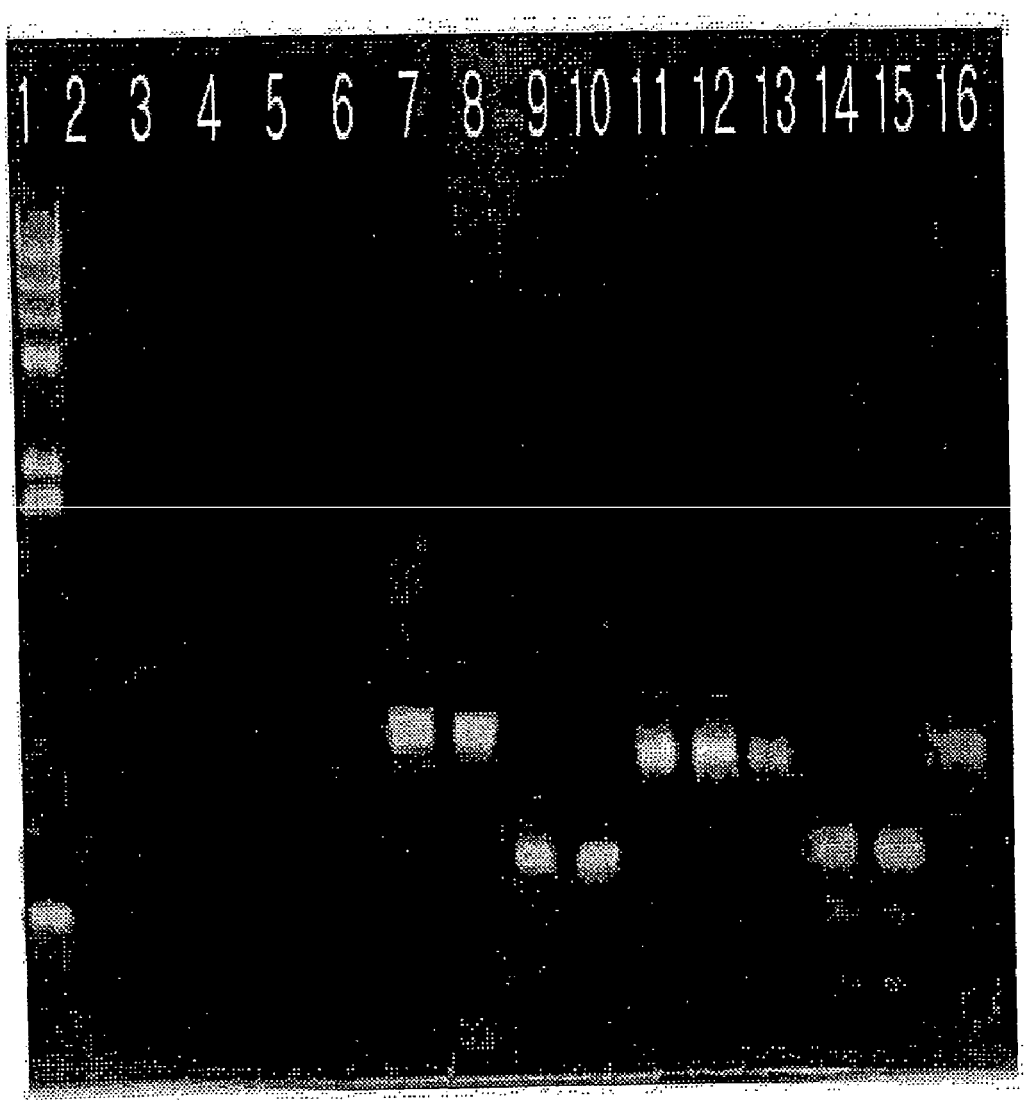
FIG. 6 is a photograph of an agarose gel showing the expression of mRNA for CPS I, OTC, AS, AL and ARG genes in a CHO cell simultaneously transformed with expression vectors pCIneo-CPS45, pREP4-OTC1, pc3.1/Zeo(+)-AS, pc3.1/Zeo(+)-AL and pc3.1/Zeo(+)-ARG in which lane 1 represents lambda phage DNA fragments digested with HindIII (restriction enzyme) as a size marker; lanes 2 to 6 represent RT-PCR amplified products using a total RNA extracted from a CHO-neo-5 cell line, namely, the amplified products of CPS I (lane 2), OTC (lane 3), AS (lane 4), AL (lane 5) and ARG (lane 6) mRNAs; lanes 7 to 11 represent the RT-PCR amplified products of CPS I, OTC, AS, AL and ARG mRNAs using a total RNA extracted from a CHO-ARG-11 cell line, respectively; lanes 12, 13, 14 and 16 represent the RT-PCR amplified products of CPS I, OTC, AS and ARG mRNAs using a total RNA extracted from rat liver, respectively; and lane 15 represents PCR products using pc3.1/Zeo(+)-AL and AL primers.

The amplification results for CPS1, OTC, AS in a CHO-AS-16 cell line, CPS1, OTC, AS and AL in a CHO-AL-19 cell line, and CPS1, OTC, AS, AL and ARG in a CHO-ARG-11 cell line were shown in FIGS. 4, 5, and 6, respectively. Analysis for RT-PCR products on agarose gel electrophoresis showed the expected size for CPS1 (1 kb), OTC (1 kb), AS (750 bp), AL (750 bp) and ARG (970 bp). These results indicate that CPS I, OTC and AS were simultaneously expressed in CHO-AS-16 cell line (FIG. 4), CPS I, OTC, AS and AL were simultaneously expressed in CHO-AL-19 cell line (FIG. 5) and CPS I OTC, AS, AL and ARG were simultaneously expressed in CHO-ARG-11 cell line (FIG. 6). Especially, the expression levels of CPS1 and OTC were the highest in a CHO-AL-19 cell line.

EXAMPLE 11

Measurement of Intracellular Ammonia Removing Ability

Ammonia concentrations in the culture media were measured to evaluate the ability of the cell lines established in this invention for their ammonia removing ability. Cells expressing CPS I and OTC (CHO-OTC1-A19), cells expressing CPS I, OTC and AS (CHO-AS-16), cells expressing CPS I, OTC, AS and AL (CHO-AL-19), and cells expressing CPS I, OTC, AS, AL and ARG (CHO-ARG-11) were inoculated at a denstity of $1 \times 10^5$ cells/ml into a six-well plates containing 2.5 ml of the culture medium. CHO-neo-5 was also included as a negative control. To provide cofactors necessary to CPS I and OTC activities, 1 mM N-carbamoyl-L-glutamate and 5 mM L-ornithine were added to media for the culture of each cell lines (Ref. Grisolia and Cohen, J. Biol. Chem. 204, 753–757, 1953; Kim et al., Proc. Nat. Acad. Sci USA 69, 3530–3533, 1972; Fahien et al., J. Biol. Chem. 239, 1935–1941, 1964; and Greenstein and Winitz, Chemistry of the Amino Acids, vol. 2, Wiley, New York, pp. 1751–1758, 1961). A previous experiment showed that the addition of the cofactors had no effect on the accumulation of ammonium ions.

One ml of the culture media was collected every 24 hours for six days and each collection was stored at –20° C. until use. To prepare standard ammonia solutions, 500 mM $NH_4Cl$ stock solution was diluted to 0, 1, 3 and 5 mM $NH_4Cl$. The ammonia concentration was measured by a modified indophenol method (Ref. Wakisaka et al., Anal. Biochem. 163, 117–122, 1987). To remove the inhibitor for colorimetric reactions, 640 μl of a protein removing reagent containing 1% sodium tungstate and 0.1N sulfuric acid was mixed to the sample collected from the culture media or 160 μl of the standard solutions. After adding 1 ml of the reagent I (5 g of phenol and 25 mg sodium nitroprusside (Na$_2$[Fe(CN)$_5$NO]$_2$H$_2$O)/500 ml) into the mixture, 1 ml of a reagent II (5 g of NaOH and 53.6 g of Na$_2$HPO$_4$12H$_2$O and 10 ml chlorine 10% per liter) was added. The reaction mixture was kept at 37° C. for 20 minutes and then cooled by incubating them in ice-cold water for 5 minutes to stop the reaction. Two hundred ul of the reaction mixture was added to the well of 96-well plate and OD value was measured at 630 nm. Ammonia concentration was calculated based on the OD value at 630 nm.

The results showed that the CHO-OTC1-A19 cell line had a lower ammonia accumulation than the control, CHO-neo-5 by about 25 to 33% (See FIG. 7).

From 96 hours after culture, the CHO-AS-16 cell line started to show a lower ammonia accumulation than the negative control, CHO-neo-5 by about 30 to 40% and than the CHO-OCT1-A19 cell line by about 2 to 3%. After 96 to 144 hours of CHO-neo-5 by more than 40% on average and than the CHO-OTC1-A19 by about 15%. The CHO-ARG-11 cell line also had a lower ammonia accumulation than CHO-neo-5 by about 40 to 50% on average and than the CHO-OTC1-A19 by about 15% (See FIG. 7).

EXAMPLE 12

Measurement of Growth Rate of Cells

To measure the cell growth rate, trypsin was added to the cells to prepare a cell suspension after media was taken for the ammonia assay as described in Example 11. This cell suspension was mixed with 0.4% (w/v) of Trypan Blue at 1:1 (v/v) and viable cells in the cell suspension were counted with a hemacytometer.

The results showed that the CHO-OTC1-A19 cell had a higher growth rate than the control, CHO-neo-5 (See FIG. 8).

Both the CHO-AS-16 and the CHO-AL-19 showed a higher growth rate than the negative cell line, CHO-neo-5. More specifically, the number of viable cells in the CHO-AS-16 became higher than that in the CHO-neo-5 after 96 hours of culture started so that, after 144 hours of culture, the CHO-AS-16 had a higher growth rate than the CHO-neo-5 by 36% and than the CHO-OTC1-A19 by about 3%. The number of viable cells in the CHO-AL-19 became higher than that in the CHO-neo-5 since 96 hours of culture so that, after 144 hours of culture, the CHO-AL-19 had a higher growth rate than the CHO-neo-5 by 44% and than the CHO-OTC1-A19 by about 10%. The number of viable cells in the CHO-ARG-11 began to be higher than that in the CHO-neo-5 since 120 hours of culture. CHO-ARG-11 had a higher growth rate than the CHO-neo-5 by about 16% and lower than the CHO-OTC1-A19 by about 7 to 10% after 144 hours.

EXAMPLE 13

Measurement of Ammonia Concentration in the Media Per Cell

Based on the ammonia concentration and the number of viable cells measured in Examples 12 and 13, the ammonia concentration in the culture media per cell was calculated and plotted in the graph shown in FIG. 9. Since 96 hours of culture at which cell population became 100% confluency, the CHO-AS-16 cell line had a lower ammonia concentration per cell than the CHO-neo-5 by about 40 to 50% and than the CHO-OTC1-A19 by about 6%. The CHO-AL-19 cell line also had a lower ammonia concentration per cell than the CHO-neo-5 by about 45 to 60% and than the CHO-OTC1-A19 by about 20%. The CHO-ARG-11 cell line showed a lower ammonia concentration per cell than the CHO-neo-5 by about 35 to 50% after 96 hours of culture and than the CHO-OTC1-A19 by about 4 to 6% after 122 to 144 hours of culture.

Ammonia is constantly produced as a waste material through various catabolic metabolism during the cell culture and a part of ammonia produced is reused in the biosyntheses of amino acids, nucleic acids or lipids at the same time. Accordingly, it can be seen that the ammonia concentration in the medium at certain time points reflects a net results of catabolism and ammonia-removing mechanism. The cell lines expressing urea cycle enzymes in the present invention are considered to have a strong ammonia removing ability due to the introduction of another ammonia-removing mechanism, that is, the urea cycle, compare to the CHO cell line transformed only with the control vector. Therefore, cell lines expressing enzymes participating in the first and second steps, the first to third steps, the first to fourth steps, or the first to fifth steps of the urea cycle are expected to have a higher growth rate of cells relative to the control cell.

Compared to the cell lines expressing enzymes involved in the first and second steps, the first to third steps, or the first to fourth steps of the urea cycle, the cell line expressing all five enzymes has a lower ammonia concentration and, unlike the expectation, a lower growth rate of cells. The reason for this may lie in that over-expression of arginase in CHO cells unnecessarily degrades the arginine added to the medium as an essential amino acid for the cell growth, thereby cell becomes arginine-deficient and show slow growth rate.

EXAMPLE 14

Effect on the Production of Proteins

In order to examine if the introduction of ammonia removing ability to CHO cells improves the productivity of recombinant proteins in cultures, CPS I, OTC, AS, and AL expression plasmids obtained in Example 1, 2, 3, and 4, respectively, were introduced into EPO (erythropoitin) producing CHO cells with the same method used in Example 6. The results reveal that the yield of EPO increases 20 μg to 60 μg per ml medium and the amount of sialic acid in EPO maintains 10% or more. It shows that introduction of genes for urea cycle enzymes into CHO cells improves the ammonia removing ability and cell viability and then increases the yield of the proteins and maintain the activity of the proteins.

INDUSTRIAL APPLICABILITY

As described above, the animal cells transformed with both CPS I and OTC expression plasmids, all of CPS I, OTC and AS expression plasmids, all of CPS I, OTC, AS and AL expression plasmids, or all of CPS I, OTC, AS, AL and ARG expression plasmids have a low ammonia accumulation in the culture medium as well as a high cell growth rate, and thus are effective in over-expression of proteins.

The invention claimed is:

1. An expression vector pCIneo-CPS45 (KCTC 0846BP) containing a rat CPS I gene for transforming an animal cell to be used in over-expression of proteins.

2. An expression vector pREP4-OTC1 (KCTC 0847BP) containing a rat OTC gene for transforming an animal cell to be used in over-expression of proteins.

3. An isolated CHO (Chinese Hamster Ovary) cell transformed with both an expression vector, pCIneo-CPS45 (KCTC 0846BP) containing a CPS I (carbamoyl phosphate synthetase I) gene and an expression vector, pREP4-OTC1 (KCTC 0847BP) containing an OTC (ornithine transcarbamoylase) gene.

4. An isolated CHO cell simultaneously transformed with an expression vector, pCIneo-CPS45 (KCTC 0846BP) containing a CPS I gene, an expression vector, pREP4-OTC1 (KCTC 0847BP) containing an OTC gene, and an expression vector, pc3.1/Zeo(+)-AS (KCTC 10014BP) containing an AS (arginosuccinate synthetase) gene.

5. An isolated CHO cell simultaneously transformed with an expression vector, pCIneo-CPS45 (KCTC 0846BP) containing a CPS I gene, an expression vector, pREP4-OTC1 (KCTC 0847BP) containing an OTC (ornithine transcarbamoylase) gene, an expression vector, pc3.1/Zeo(+)-AS (KCTC 10014BP) containing an AS gene, and an expression vector, pc3.1/Zeo(+)-AL (KCTC 10013BP) containing an AL (arginosuccinate lyase) gene.

6. An isolated CHO cell simultaneously transformed with an expression vector, pCIneo-CPS45 (KCTC 0846BP) containing a CPS I gene, an expression vector, pREP4-OTC1 (KCTC 0847BP) containing an OTC gene, an expression vector, pc3.1/Zeo(+)-AS (KCTC 10014BP) containing an AS gene, an expression vector, pc3.1/Zeo(+) -AL (KCTC 10013BP) containing an AL gene, and an expression vector, pc3. 1/Zeo(+)-Arg (KCTC 10012BP) containing an ARG (arginase) gene.

7. The CHO cell as claimed in claim 3, wherein the CHO cell is CHO-OTC1-A19 (CHO/dhfr$^-$) (KCTC 0845BP).

8. The CHO cell as claimed in claim 7, wherein the CHO cell is CHO-AS-16 (CHO/dhfr$^-$) (KCTC 1003 IBP).

9. The CHO cell as claimed in claim 5, wherein the CHO cell is CHO-AL-19 (CHO/dhfr$^-$) (KCTC 10015BP).

10. The CHO cell as claimed in claim 6, wherein the CHO cell is CHO-Arg-11 (CHO/dhfr$^{31}$ ) (KCTC 100300BP).

* * * * *